US008722343B2

(12) United States Patent
Perego et al.

(10) Patent No.: US 8,722,343 B2
(45) Date of Patent: May 13, 2014

(54) METHODS AND COMPOSITIONS FOR THE DIAGNOSIS AND TREATMENT OF DIABETES

(75) Inventors: Carla Perego, Usmake Velate (IT); Eliana Sara Di Cairano, Milan (IT); Alberto Davalli, Milan (IT); Franco Folli, San Antonio, TX (US)

(73) Assignees: Carla Perego, Usmate Velate (IT); Alberto Davalli, Milan (IT); Franco Folli, San Antonio, TX (US)

( * ) Notice: Subject to any disclaimer, the term of this patent is extended or adjusted under 35 U.S.C. 154(b) by 11 days.

(21) Appl. No.: 13/130,196

(22) PCT Filed: Nov. 20, 2009

(86) PCT No.: PCT/EP2009/008256
§ 371 (c)(1),
(2), (4) Date: May 19, 2011

(87) PCT Pub. No.: WO2010/057647
PCT Pub. Date: May 27, 2010

(65) Prior Publication Data
US 2011/0244486 A1     Oct. 6, 2011

Related U.S. Application Data

(60) Provisional application No. 61/116,866, filed on Nov. 21, 2008.

(51) Int. Cl.
*G01N 33/48*    (2006.01)
*G01N 33/49*    (2006.01)
*G01N 33/53*    (2006.01)

(52) U.S. Cl.
USPC ........................................................ 435/7.1

(58) Field of Classification Search
None
See application file for complete search history.

(56) References Cited

U.S. PATENT DOCUMENTS

| | | | |
|---|---|---|---|
| 6,074,828 A | 6/2000 | Amara et al. | |
| 2007/0218519 A1 | 9/2007 | Urdea et al. | |

FOREIGN PATENT DOCUMENTS

| | | |
|---|---|---|
| EP | 0 200 412 A2 | 11/1986 |
| WO | WO 9204632 A1 | 3/1992 |

OTHER PUBLICATIONS

Boston-Howes, W. et al., "Nordihydroguaiaretic acid increases glutamate uptake in vitro and in vivo: Therapeutic implications for amyotrophic lateral sclerosis." Experimental Neurology, Academic Press, New York, NY, US, vol. 213, No. 1, Sep. 1, 2008, pp. 229-23, XP024100583, ISSN: 0014-4886.
Winter, William E., et al., "Type 1 diabetes islet autoantibody markers." Diabetes Technology & Therapeutics 2002, vol. 4, No. 6, 2002, pp. 817-839, XP002575517, ISSN: 1520-9156.
Schmidt, K. D. et al., "Autoantibodies in Type 1 diabetes." Clinica Chimica Acta, Elsevier BV, Amsterdam, NL, vol. 354, No. 1-2, Apr. 1, 2005, pp. 35-40, XP004770124, ISSN: 0009-8981.
Manfras, B. J. et al., "Cloning and characterization of glutamate transporter cDNA from human brain and pancreas." Biochimica ET Biophysica Acta Biomembranes, Amsterdam, NL, vol. 1195, No. 1, Oct. 12, 1994, pp. 185-188, XP02335429, ISSN: 0005-2736.
Manfras, B. J. et al., "Expression of a glutamate transporter cDNA in human pancreatic islets." Experimental and Clinical Endocrinology & Diabetes: official Journal, German Society of Endocrinology [and] German Diabetes Association 1995, vol. 103 Suppl 2, 1995, pp. 95-98, XP8120781, ISSN: 0947-7349.
Boehm B. O., et al., "Lack of L-glutamate transporter transcription in human pancreatic islets." Diabetologia, vol. 36, No. Suppl. 1, 1993, p. A80, XP008120776 & 29th Anual Meeting of the European Association for the Study of Diabetes; Istanbul, Turkey; Sep. 6-10, 1993, ISSN: 0012-186X.
Lee, Seung-Hee et al., "Cytoprotective effects of polyenoylphosphatidylcholine (PPC) on beta-cells during diabetic induction by streptozotocin." The Journal of Histochemistry and cytochemistry; Official Journal of the Histochemistry Society Aug. 2003, pp. 1005-1015, XP002575519, ISSN: 0022-1554.
Toyoda et al., "GLP-1 receptor signaling protects pancreatic beta cells in intraportal islet transplant by inhibiting apoptosis." Biochemical and Biophysical Research Communications, Academic Press Inc. Orlando, FL, US, vol. 367, No. 4, Jan. 22, 2008, pp. 793-798, XP022449875. ISSN: 0006-291X.
Pileggi, A., et al., "Protecting Pancreatic .Beta. -Cells." IUBMB Life, Taylor and Francis, London, GB, vol. 56, No. 7, Jan. 1, 2004, pp. 387-394, XP008068163, ISSN: 1521-6543.
Roisin-Bouffay, C., et al., "Mouse Vanin-1 is cytoprotective for islet beta cells and regulates the development of type 1 diabetes" Diabetologia; Clinical and Experimental Diabetes and Metabolism, Springer, Berlin, DE, vol. 51, No. 7, May 8, 2008, pp. 1192-1201, XP019618442, ISSN: 1432-0428.

*Primary Examiner* — Michael Pak
(74) *Attorney, Agent, or Firm* — Lucas & Mercanti, LLP

(57) ABSTRACT

Methods, assays and compositions for the diagnosis and treatment of diabetes, in which the glutamate transporters and/or receptors expressed in pancreatic islet cells are used as therapeutic targets or tools for the identification or treatment of individuals suffering from or susceptible to diabetes.

4 Claims, 11 Drawing Sheets

SEQUENCE LISTING

<160> NUMBER OF SEQ ID NOS: 14

<210> SEQ ID NO 1
<211> LENGTH: 574
<212> TYPE: PRT
<213> ORGANISM: Homo sapiens

<400> SEQUENCE: 1

```
Met Ala Ser Thr Glu Gly Ala Asn Asn Met Pro Lys Gln Val Glu Val
1               5                   10                  15

Arg Met His Asp Ser His Leu Gly Ser Glu Glu Pro Lys His Arg His
                20                  25                  30

Leu Gly Leu Arg Leu Cys Asp Lys Leu Gly Lys Asn Leu Leu Leu Thr
            35                  40                  45

Leu Thr Val Phe Gly Val Ile Leu Gly Ala Val Cys Gly Gly Leu Leu
        50                  55                  60

Arg Leu Ala Ser Pro Ile His Pro Asp Val Val Met Leu Ile Ala Phe
65                  70                  75                  80

Pro Gly Asp Ile Leu Met Arg Met Leu Lys Met Leu Ile Leu Pro Leu
                85                  90                  95

Ile Ile Ser Ser Leu Ile Thr Gly Leu Ser Gly Leu Asp Ala Lys Ala
                100                 105                 110

Ser Gly Arg Leu Gly Thr Arg Ala Met Val Tyr Tyr Met Ser Thr Thr
            115                 120                 125

Ile Ile Ala Ala Val Leu Gly Val Ile Leu Val Leu Ala Ile His Pro
        130                 135                 140

Gly Asn Pro Lys Leu Lys Lys Gln Leu Gly Pro Gly Lys Lys Asn Asp
145                 150                 155                 160

Glu Val Ser Ser Leu Asp Ala Phe Leu Asp Leu Ile Arg Asn Leu Phe
                165                 170                 175

Pro Glu Asn Leu Val Gln Ala Cys Phe Gln Gln Ile Gln Thr Val Thr
                180                 185                 190

Lys Lys Val Leu Val Ala Pro Pro Asp Glu Glu Ala Asn Ala Thr
            195                 200                 205

Ser Ala Val Val Ser Leu Leu Asn Glu Thr Val Thr Glu Val Pro Glu
        210                 215                 220

Glu Thr Lys Met Val Ile Lys Lys Gly Leu Glu Phe Lys Asp Gly Met
225                 230                 235                 240

Asn Val Leu Gly Leu Ile Gly Phe Phe Ile Ala Phe Gly Ile Ala Met
                245                 250                 255
```

Gly Lys Met Gly Asp Gln Ala Lys Leu Met Val Asp Phe Phe Asn Ile
            260                 265                 270

Leu Asn Glu Ile Val Met Lys Leu Val Ile Met Ile Met Trp Tyr Ser
        275                 280                 285

Pro Leu Gly Ile Ala Cys Leu Ile Cys Gly Lys Ile Ile Ala Ile Lys
    290                 295                 300

Asp Leu Glu Val Val Ala Arg Gln Leu Gly Met Tyr Met Val Thr Val
305                 310                 315                 320

Ile Ile Gly Leu Ile Ile His Gly Gly Ile Phe Leu Pro Leu Ile Tyr
                325                 330                 335

Phe Val Val Thr Arg Lys Asn Pro Phe Ser Phe Ala Gly Ile Phe
            340                 345                 350

Gln Ala Trp Ile Thr Ala Leu Gly Thr Ala Ser Ser Ala Gly Thr Leu
        355                 360                 365

Pro Val Thr Phe Arg Cys Leu Glu Glu Asn Leu Gly Ile Asp Lys Arg
    370                 375                 380

Val Thr Arg Phe Val Leu Pro Val Gly Ala Thr Ile Asn Met Asp Gly
385                 390                 395                 400

Thr Ala Leu Tyr Glu Ala Val Ala Ala Ile Phe Ile Ala Gln Met Asn
                405                 410                 415

Gly Val Val Leu Asp Gly Gly Gln Ile Val Thr Val Ser Leu Thr Ala
            420                 425                 430

Thr Leu Ala Ser Val Gly Ala Ala Ser Ile Pro Ser Ala Gly Leu Val
        435                 440                 445

Thr Met Leu Leu Ile Leu Thr Ala Val Gly Leu Pro Thr Glu Asp Ile
    450                 455                 460

Ser Leu Leu Val Ala Val Asp Trp Leu Leu Asp Arg Met Arg Thr Ser
465                 470                 475                 480

Val Asn Val Val Gly Asp Ser Phe Gly Ala Gly Ile Val Tyr His Leu
                485                 490                 495

Ser Lys Ser Glu Leu Asp Thr Ile Asp Ser Gln His Arg Val His Glu
            500                 505                 510

Asp Ile Glu Met Thr Lys Thr Gln Ser Ile Tyr Asp Asp Met Lys Asn
        515                 520                 525

His Arg Glu Ser Asn Ser Asn Gln Cys Val Tyr Ala Ala His Asn Ser
    530                 535                 540

Val Ile Val Asp Glu Cys Lys Val Thr Leu Ala Ala Asn Gly Lys Ser
545                 550                 555                 560

Ala Asp Cys Ser Val Glu Glu Glu Pro Trp Lys Arg Glu Lys
                565                 570

<210> SEQ ID NO 2
<211> LENGTH: 569
<212> TYPE: PRT
<213> ORGANISM: Mus musculus

<400> SEQUENCE: 2

Met Val Ser Ala Asn Asn Met Pro Lys Gln Val Glu Val Arg Met His
1               5                   10                  15

Asp Ser His Leu Ser Ser Asp Glu Pro Lys His Arg Asn Leu Gly Met
            20                  25                  30

Arg Met Cys Asp Lys Leu Gly Lys Asn Leu Leu Ser Leu Thr Val
        35                  40                  45

Phe Gly Val Ile Leu Gly Ala Val Cys Gly Gly Leu Leu Arg Leu Ala
    50                  55                  60

-continued

```
Ser Pro Ile His Pro Asp Val Val Met Leu Ile Ala Phe Pro Gly Asp
 65                  70                  75                  80

Ile Leu Met Arg Met Leu Lys Met Leu Ile Leu Pro Leu Ile Ile Ser
                 85                  90                  95

Ser Leu Ile Thr Gly Leu Ser Gly Leu Asp Ala Lys Ala Ser Gly Arg
            100                 105                 110

Leu Gly Thr Arg Ala Met Val Tyr Tyr Met Ser Thr Ile Ile Ala
        115                 120                 125

Ala Val Leu Gly Val Ile Leu Val Leu Ala Ile His Pro Gly Asn Pro
    130                 135                 140

Lys Leu Lys Lys Gln Leu Gly Pro Gly Lys Lys Asn Asp Glu Val Ser
145                 150                 155                 160

Ser Leu Asp Ala Phe Leu Asp Leu Ile Arg Asn Leu Phe Pro Glu Asn
                165                 170                 175

Leu Val Gln Ala Cys Phe Gln Gln Ile Gln Thr Val Thr Lys Lys Val
            180                 185                 190

Leu Val Ala Pro Pro Ser Glu Glu Ala Asn Thr Thr Lys Ala Val Ile
        195                 200                 205

Ser Met Leu Asn Glu Thr Met Asn Glu Ala Pro Glu Glu Thr Lys Ile
    210                 215                 220

Val Ile Lys Lys Gly Leu Glu Phe Lys Asp Gly Met Asn Val Leu Gly
225                 230                 235                 240

Leu Ile Gly Phe Phe Ile Ala Phe Gly Ile Ala Met Gly Lys Met Gly
                245                 250                 255

Glu Gln Ala Lys Leu Met Val Glu Phe Phe Asn Ile Leu Asn Glu Ile
            260                 265                 270

Val Met Lys Leu Val Ile Met Ile Met Trp Tyr Ser Pro Leu Gly Ile
        275                 280                 285

Ala Cys Leu Ile Cys Gly Lys Ile Ile Ala Ile Lys Asp Leu Glu Val
    290                 295                 300

Val Ala Arg Gln Leu Gly Met Tyr Met Ile Thr Val Ile Val Gly Leu
305                 310                 315                 320

Ile Ile His Gly Gly Ile Phe Leu Pro Leu Ile Tyr Phe Val Val Thr
                325                 330                 335

Arg Lys Asn Pro Phe Ser Phe Phe Ala Gly Ile Phe Gln Ala Trp Ile
            340                 345                 350

Thr Ala Leu Gly Thr Ala Ser Ser Ala Gly Thr Leu Pro Val Thr Phe
        355                 360                 365

Arg Cys Leu Glu Asp Asn Leu Gly Ile Asp Lys Arg Val Thr Arg Phe
    370                 375                 380

Val Leu Pro Val Gly Ala Thr Ile Asn Met Asp Gly Thr Ala Leu Tyr
385                 390                 395                 400

Glu Ala Val Ala Ala Ile Phe Ile Ala Gln Met Asn Gly Val Ile Leu
                405                 410                 415

Asp Gly Gly Gln Ile Val Thr Val Ser Leu Thr Ala Thr Leu Ala Ser
            420                 425                 430

Ile Gly Ala Ala Ser Ile Pro Ser Ala Gly Leu Val Thr Met Leu Leu
        435                 440                 445

Ile Leu Thr Ala Val Gly Leu Pro Thr Glu Asp Ile Ser Leu Leu Val
    450                 455                 460

Ala Val Asp Trp Leu Leu Asp Arg Met Arg Thr Ser Val Asn Val Val
465                 470                 475                 480

Gly Asp Ser Phe Gly Ala Gly Ile Val Tyr His Leu Ser Lys Ser Glu
                485                 490                 495
```

Leu Asp Thr Ile Asp Ser Gln His Arg Met Gln Glu Asp Ile Glu Met
                500                 505                 510

Thr Lys Thr Gln Ser Ile Tyr Asp Asp Lys Asn His Arg Glu Ser Asn
            515                 520                 525

Ser Asn Gln Cys Val Tyr Ala Ala His Asn Ser Val Val Ile Asp Glu
        530                 535                 540

Cys Lys Val Thr Leu Ala Ala Asn Gly Lys Ser Ala Asp Cys Ser Val
545                 550                 555                 560

Glu Glu Glu Pro Trp Lys Arg Glu Lys
                565

<210> SEQ ID NO 3
<211> LENGTH: 12021
<212> TYPE: DNA
<213> ORGANISM: Homo sapiens

<400> SEQUENCE: 3

```
gggtgatgtc agctctcgac gaaaatagag agggatcgcc tgcaaatccc cagctccggc      60
ggggctaaac cttgcaatcc ctccctggcc ggcgccgagc cagagcgcag cggcctccac     120
cgcctcccca ggcgcgcaca cacccgcaca cgcgcacgca cgctcaccgt cctctgccac     180
cactctctgc tcccgccact cgccgcgccc gcgagccccg cagcaaagca caggtggcag     240
cggctgcagg ggcgcatcgc cggcgtgcgc cctcctgcag ccctgggcgc atcgctctct     300
cggggaagcc accctcggag cccccggagc tccccgccaa cgccatccc cgcgggcgga      360
ggggagcgcg ggtcgcgcgc cgtggagagc cgggacgcgg attagcgccc gcaggagcct     420
cctgcgcccg ttgaggcgct aaagggctta ccccggaggc gggtggaagg gcgggcagag     480
gctcctctta ataccgctc ccggccgcac ttcgcgctca ccccggcgtc cgctttctcc      540
ctcgcccaca gctgccggat agtgctgaag aggaggggc gttccccaga ccatggcatc     600
tacggaaggt gccaacaata tgcccaagca ggtggaagtg cgaatgcacg acagtcatct     660
tggctcagag gaacccaagc accggcacct gggcctgcgc ctgtgtgaca agctggggaa     720
gaatctgctg ctcaccctga cggtgtttgg tgtcatcctg ggagcagtgt gtggagggct     780
tcttcgcttg gcatctccca tccaccctga tgtggttatg ttaatagcct cccagggga     840
tatactcatg aggatgctaa aaatgctcat tctccctcta atcatctcca gcttaatcac     900
agggttgtca ggcctggatg ctaaggctag tggccgcttg ggcacgagag ccatggtgta     960
ttacatgtcc acgaccatca ttgctgcagt actgggggtc attctggtct ggctatcca    1020
tccaggcaat cccaagctca gaagcagct ggggcctggg aagaagaatg atgaagtgtc    1080
cagcctggat gccttcctgg accttattcg aaatctcttc cctgaaaacc ttgtccaagc    1140
ctgctttcaa cagattcaaa cagtgacgaa gaaagtcctg gttgcaccac cgccggacga    1200
ggaggccaac gcaaccagcg ctgttgtctc tctgttgaac gagactgtga ctgaggtgcc    1260
ggaggagact aagatggtta tcaagaaggg cctggagttc aaggatggga tgaacgtctt    1320
aggtctgata gggtttttca ttgcttttgg catcgctatg gggaagatgg agatcaggc    1380
caagctgatg gtggatttct tcaacatttt gaatgagatt gtaatgaagt tagtgatcat    1440
gatcatgtgg tactctcccc tgggtatcgc ctgcctgatc tgtggaaaga tcattgcaat    1500
caaggactta gaagtggttg ctaggcaact ggggatgtac atggtaacag tgatcatagg    1560
cctcatcatc cacggggggca tctttctccc cttgatttac tttgtagtga ccaggaaaaa    1620
ccccttctcc ttttttgctg gcattttcca agcttggatc actgccctgg gcaccgcttc    1680
```

```
cagtgctgga actttgcctg tcacctttcg ttgcctggaa gaaaatctgg ggattgataa    1740
gcgtgtgact agattcgtcc ttcctgttgg agcaaccatt aacatggatg gtacagccct    1800
ttatgaagcg gtagccgcca tctttatagc ccaaatgaat ggtgttgtcc tggatggagg    1860
acagattgtg actgtaagcc tcacagccac cctggcaagc gtcggcgcgg ccagtatccc    1920
cagtgccggg ctggtcacca tgctcctcat tctgacagcc gtgggcctgc aacagagga    1980
catcagcctg ctggtggctg tggactggct gctggacagg atgagaactt cagtcaatgt    2040
tgtgggtgac tcttttgggg ctgggatagt ctatcacctc tccaagtctg agctggatac    2100
cattgactcc cagcatcgag tgcatgaaga tattgaaatg accaagactc aatccattta    2160
tgatgacatg aagaaccaca gggaaagcaa ctctaatcaa tgtgtctatg ctgcacacaa    2220
ctctgtcata gtagatgaat gcaaggtaac tctggcagcc aatggaaagt cagccgactg    2280
cagtgttgag gaagaacctt ggaaacgtga gaaataagga tatgagtctc agcaaattct    2340
tgaataaact ccccagcgta tcctatggta actgatgata taaacaagct ttctttaaaa    2400
aggaaaaaaa tgcgtatatt tctatgttta cttaatctgt tagccgaggc ttagaggagc    2460
tcttgtgagt cagtgatgac aggcacggtg ctgtgtcttt gccaaataat gcttataac    2520
cgtctaattt tctcacttgt attattattt gaatggatgc tgctggagga atcagttgga    2580
attgaagaca cgttcttgcc agcttcccct ttctcccaag atgcagaaat gtggatgctc    2640
ttttcccagg ggacatgagt aaagcagtgt ggtacactcc agggacttgg gaaaatgagc    2700
aaacacacag cgtgttattc cttaaagtgt tctccatgtc tcgccttgtt atgcacaaga    2760
gattctatta aaagcctcta gaagtaactc cccttaaaat gtctagtaaa gcttgcacat    2820
ggattgatta aaagcaaata cctgtcttag ggaattctga caatttatct tccatatgct    2880
ctttaagtaa aatgtttcaa agacagtttt aaagggagcc atgctcttaa aggcagttga    2940
ttaaagaacc tgttacatct ctgccttacc ctgtgtaatc tgtgagaaca atggttgaaa    3000
tttcaaagta tgtttcatta ttcttttctaa atttgataat tgattaggaa gtattttata    3060
tataaccact gtagatattg acaaaagtaa gagagcacag tcaacataaa gtttaaccag    3120
agttaaatat tcaaatttat ttatgttcgg tttgccttca cctggtgtag taaaatcaaa    3180
tgagattatt tggtatgtgt tttgctttgt ttaacccaaa agattatttt ttggttccta    3240
aagaaaaaga tatttttaat ctgtcaatta tttcagtcat catctcatcg tcctagaaag    3300
cctggtcatt ttactgtcct cacacatgga agacacttgt gttggctgtg cctctttta    3360
tgtcatctct tgatgaaaca aaaatactgg tatttatcca atatgttgaa agcgttttgt    3420
tatcttctat caaagcacat aaaaccagtt ataggacaca gttggaagca gagccagtct    3480
tcctcctcag tcttctcagt agaaaggaac agaaaacaaa catctgtgca aaaccctata    3540
aaagtgatat tcctatggca gagtccaggc agccttgaac aatgacatgg caacaaagga    3600
tggctctgta caacttcaca gatggaatct tgtttaaggc tgtgaagttt taaggaataa    3660
ataatataat tggtgtagca cagtgccttg catgcagtag gcagccaaca aatccttaat    3720
gattggtaat gcaagctaaa attttaatg tctctactat cctttttat tgaataacgc    3780
acagtatttt cctaaggttg ctgggtttgg gagtaagctt gggacttgaa tcattgagaa    3840
ataaagcaca tttgactcta agaagtatgt agaaccttgt ttataggtga gataggctg    3900
tattatatga aaccagcgga gggatgctga gacagtcatg gtttatagaa tccaaattct    3960
ctgagatgag ggtgcttatg gacctcaaat agcctttctt atctgctcct tgtgacttct    4020
ctctttaaa tcagatacct ttgaaacata caagagacat gagattccag ttgttttgt    4080
```

```
ctcctaaacc ctagtgattt ttggataagg atcactactg aacagtatta ggcaactttt   4140 cattttttgct tttcaaatga cattggtctt tatttccagt agatgggcag taaacagggt   4200
cagggtggtc aagggatatg attaagtgta gtagtagaaa atgcattctt tttttttttt   4260 ttttttaga cagagtcttg ctctgttgct caggctggag tacagtggca cgatctcagc   4320
tcactgcact gcaatgtcca cctctctagt tcaagcgatt ctcctgtctc agcctcccga   4380
gtagctggga ctacaggcac atgccaccat gcctggctaa ttttttgtat ttttagtaca   4440
gatgggtttc attatgttag ccaggatggt ctcgatctcc tgacctcatg atccacccgc   4500
catgccctcc caaagtgctg ggattacagg cgtgagccac cgtgcccggc cagaaaatac   4560
attctttaca gcaaatgtta taggttaagg agacagttcc tgggtttagc tgtgaaactg   4620
tttaggattt tctttaagtg gtgttcccaa gagctttttt ctggtaagtt ggaggctata   4680
ggcaaagcgt ctaggagctt gttgtttttt gctatggaag gccagctttg ggatctatat   4740
acatgggcat gtttctcaat ggagtggtca caggattctc ttctcagaac tctgcctgaa   4800 accttttccgg tgtgttttgt cttcaacttt ttcctagcta tcctattagc ctgtaaatat   4860
gtcagcagac aatgtgtttg gaagaaacaa ggtgtacaac ttcacaaagc aagttttttc   4920
tggtctgaga cttactgtgt gcaggaagtc tcgtgagaat atacttagaa aatcacactt   4980
atctggaaat tcaataagtc atattaaaaa tatacaattt cttgaactca ggactagcct   5040
gaaaatccaa aatgcatgta gagttgacat gttgacatat gtctatgtcc tctgttttta   5100
tttaagcctc atttatttct cccttgccat gcccatttgg gatttctttt gcccagcata   5160
tgtgccataa acagaacaaa tggatccagg gtatacctct aataacccttt atctaaatag   5220 aatacattta acctgtcaat tatatgtata gatttatcct aattggttca acatatatat   5280
gaatgcttgt aatagtctgt tactatttga taatgcataa atgttatatt tatatacagt   5340
tacagcaggc cagaaacata catacactgc atcctgtaag gtctgtaaat cagggcttcg   5400
gcaatgccat tttgctatag actcattcat gttttttagg aatcagaatc atttcaggag   5460
aaaaccaact aagtagactt taattcttct ctttctcatt cttgcccttt gagaaaccca   5520
agtggaatca tcacttaatt acttactcaa attcaatgaa tcaaatccaa tccaatcagt   5580
gagaagaata gcttatcttt caaggtaata ctttacctta gatctttgag ggcatgcttc   5640
ccatacaaag agcatcagaa aatcagggca atcatctaga tctcacagat cttcaacata   5700
ggactctagg ttatgagagc tgaaccacat agctatcagt ttcagttttt acttcctatt   5760
gagtgtgtag aaaacacagcc tatggttttg ctgtctgcgg aagttaccat accctgtaaa   5820
agacaaatat ttcttttctcc tctcgaacca ctagtcagcc tggatattca tgaaagctga   5880
aagaaggggt gccaaaatgc ctagctcctg gatttagact catggaatat gagaaaggct   5940
tagggaaaat tcaagtcatg gggagattcc tgctaggtga tgccaggaat ctcaatgacc   6000
tgttgattag agggtctctg gtcatttcca cttgtgtgtg gagaaataca tcatttgcat   6060
atgtatctag tcaagaagcc cttttggagc aaagtggttg ggaaactcat ttactgggtc   6120
caccaaagga aacccaattc tgccatgttt ttgcaaatac tacacgtccc tttgctctca   6180
atagcaaaag tgatgttata gttttttttta cttttgtcag aatcaaggct tcggccacct   6240
gtgcaatatt ttcccatgga atgcagcagt aaatccaagt aggtatatcc gtgctcagag   6300
agaattctcc atagttctga ctcctgaaaa acaagtctca ttagctctca tctagtttga   6360
tgactaaaag tgcacagcag ttatacccca gtggaagtga ttttttctcac ctagctgctc   6420 tctaactctt acggctatct agttgtctga gctgctggtt tgttttactt attctccaac   6480
```

```
tgaactcatt ccaaaccaag aaaaaggacc aaatgaaatt ttcagttatt atcatacttg    6540
ctccttgaat aagaatgcta gagtctggag gcagaagaag actaagttaa aaaaaaaaca    6600
gcctgaagga attctggagt gagttttgta agtctaattg tcaaagaaga taaatggtct    6660
cagtatctgt agtaatttct ggttaagcct agagggatca ctgagtgcca atccaagcag    6720
gtggcactag aggcagattg ttctcctagc atagagtgag tttccagctg ctcatgacac    6780
attttcttat gattttccct aaaagaaaac caaattttct actccacctc ttcctttcct    6840
atcattccac ttattgttgc tgctttgcta acagccagct tagtaagcca tcacacaagt    6900
tagtgtgagg cttggtttta aaatagataa cagagaatct tgattaaata gtatccaact    6960
ttgtagcata acacagctaa ttcaggcaat gacatagaga tgataagaaa caacatggtt    7020
tggtagaggg aacatttgat ttagactctg cccattttta gctgtatgac ttacataagt    7080
cattttgtgt ccaagcctca ttttctccca tatgaaaagt gaaggggttg gattaaatga    7140
ctaaaatccc cttccagccc tatgagccca atgtattatg atctctgctt tgtttccttc    7200
ttaagaggct tcctactata aaatgtgacc tatttacatt ttaagttgaa gtagcccaca    7260
ataatgaata atcaatttag attttttctca tctccttttgg gagaaattaa attcaagcct    7320
ctattcattt gatgttttac aacaagcttc aaagttggcc atgttcattc acagtttgat    7380
attttgagac accaataaaa gttttttaat aaaagtcccc ttgacttaaa ctcaccttcc    7440
taatagaagt agtgatttgg ctcacggaaa aatgtttcca gagtcaacat gagaggactg    7500
gatgaaccta cagcctcact caagctgttg catcattgct gctgtagcaa cagagccctc    7560
tctgaatacc caaaacacac aatttttctcc aacaattcta attgcccacc cagtatggga    7620
atttgagagc ctttggtgaa taaccttgat cactcttttg aaatttggta caacacttgc    7680
acaatcacgg caactgtttg taaatatctt ttcttctccg ccagtatgta gacatgcaca    7740
cccattcaca agtaagcccg caaattcatt ttcacatttt cctcttggtt tgttttttatc    7800 atgggtatca cattgcagga agagatgctc taacttacaa gaatggaatt ttctgactat    7860
cattgccctc ttcaaggcct gattagtttg tagggtggat gggatacaat gcatggtcta    7920
caaggtccat gtcaccagcc atgatcttta aacaacctct tgcactttct ggcactgctg    7980
caatggccca tggtggacac ctctgctgtt tgtccaaact tctgctaaat agagtagtgt    8040
tggtatttgt tgtgttgtga actcctttgt tgtcagagaa gacttcagct cttcaggttt    8100
gcaagggcaa gatgtaaagc taggactgaa aggattgggt tttgttttttc ggccggcttt    8160 tttccattag tgcaaaaaac ctgatgcaag ggcagcaaga taaacacaat ttcttcattg    8220
acccagataa gaacctgtag aaaagtgaga gatgccccta agttcctatt tcatttatcc    8280
taaataatat cctgaataac tactgatcag ttttttttcta tgtccagcct tgcttcactt    8340
tccaacctcc aggccaaata ttcattttga tattttacaa aatccttctg ttttttacac    8400 agggccctttt tgtgctgaga ataaaaccag ctattggaac agacctcact gctttgtaga    8460
gtcagaagtt gacctagaga atgggtagca acaggtcctc agtttctctg gagacacccc    8520
caatccttgg gtgagtgttg aaacctgaca actgactgtt agccttgtca tcatcctcac    8580
tggagatgga gatgttgcag tcggagcctc actccttctg gggcactgtt tcttctcatg    8640
gcaaccattt tgcctgcctg gaaacagcct gttgcctttg ctaggggggca aatacacaca    8700 ctagccaagg aagttggtcc agcacatctc tgaggtttct cccccatgga cccatggagc    8760
gaattccctg agataaatga tcagaaagtt ggctgtctgg tggtttaata ctccataaga    8820
gttacttccc ttatagaaag tcatcctttg gcatctagat ttttctacaa atcacccttaa    8880
```

```
ctccctccct ttctctttct cctggaaaac ctcagcattg catctccatg ttgcacaaca   8940
cagatcagat tatctggtca ctatagagat ttgtatataa aaaaactact tttttgagga   9000
ttttgtatat tgttttttcta tttgttttct acagcttgag gaaagagctg caaactgtg    9060
aatctaactt gatcttgttg ccagcagata tattttggct tcctggtaag agtctgtgtt   9120
accagggaca atatattgcc ctctgatcag tattgcaccc taaatccaca aattcctcca   9180
gcccagtctt acatttttt aaacaaatcc cctagcttgt ttgctattat ttataaagag    9240
cattagaaaa tgtatttata gacctggatg ttatatgttt aatattaatt tagccttaa   9300
taatgttata ggtttgtaac tattcttcag aaattataaa gaactcagtg tagactgaat   9360
taatctatttt agtatctgta attttgcaga catattttct tacagtatttt tctatgtaac  9420
cacacatgta gaattataac taattagagc acaagaagtt tcttcagcaa tttagagcta   9480
ccaattgttt cttgactata tagtcacatt tgacaaattt aagaacccag tctttagtga   9540
tgcaataaac aaaatgaacc attaagaaca aggaattgct taaatccctt agctggtgag   9600
gatatacatc taaataattc atctttctaa ctcaaggaat ggtgctgatt ttttaaatgt   9660
ttgacaccag gccttgtttt tccagctgag cattctcatt ttgcttttct ctaagactat   9720
caaagacaag gtattaatag taggattatt cctagatcag aatgtttcat acattcctaa   9780
aggtttatgt ggaaattggc ttaggaaaac tttgagtagc agagactgag gatgagtgct   9840
agagatgaaa tcaggacaga tttgttgcag ttaattcttg ccaagcaaat tagtggtaaa   9900
tgtcacattg ttatgtgaat tgagcacata ttttaaaga aagtttacaa aaaattttta   9960
gaaccaacta tgaggcaata ctgtatcact ggggggctggg agtgggggct tagaatcata  10020
ctgaaattgt ttaaaagcag cccaggtagt ttctgtcctc aggtgaataa cagactatat  10080
aacttccccg aaaggtaaaa cgatagccac tgcagagacg aggtgtcttc cttccaccaa  10140
atactttctg agatggtggt aggagtagta ttttaccgt ggtttaaaaa gtagtcagtt   10200
acatagaaag tgtattggta tgtatttgaa cctgctcttc attaaacaaa cagattagat  10260
gtaccctcga ctggcaataa ttgtatctat tttcaagtac agctagctgt caaagcatga  10320
agctcttgtg tatacacact gacacttggt tcacgcatga agaacagtgc ctatgcactt  10380
tgtgtagcta taatgtaggt atctaggtgt aatttcagtg aaatggtgta tagatgtatt  10440
gtaatttaaa tgtatatgtt attttttggct attcatctaa atgcagtaga catgttgatc   10500
ggtgttttgc aaacatttct ttttccttct tagataacta gtcgtgaatc atttctcctc  10560
tttctcagtg tggcttggga atatatatga gtgaagaatt tatctgtgaa tccttgtac   10620
tgatgattgt ttgaaagtct gtgtgtgtcc agcacctttg taaatacaca attcagagca  10680
gggatgggct gggtgtgtgt cctggttctt agtgaaaggt catctcatgt ctgtttaata  10740
catggtgaat gcaactgtgg aacttttgat tacctagact taggtaggtt tagaatgaga  10800
acatccatct acagtcctcc tttgcttggt ggattgggct cagaggaaca aaaagttagt  10860
ctgactctgt gcatattagc atcatgtctt tagagaaagg tcagcctctc tggttgccaa  10920
atactcatca tgatgctcat gacttaaagg ttctgaggag ccttgtctcc cttggattt   10980
tgagtcaggg tacaggaaaa aacattgctg actaactaac tgcaaatgca tctgcaggtg  11040
aaacccctacg aaagcacagt tctggctata aacttcagg ttctctgtaa aaaacttaga  11100
gcactagaag cacaggaata gtgagtgtac agcttatgcg gttgtagagg ggcaactgat  11160
gaacacaggt cccacatata tgagggagta tgacgttctc tacctaatat gttctgtgtg  11220
catgttttga atgattgaag atgggattaa ctaatgcaag tttacagttg cctcctaaaa  11280
```

-continued

| | |
|---|---|
| cacacattct gtataattat cgctaaatac aatgctgtga ggtctatagt tcctgtaacc | 11340 |
| cctttctcct ccccaaggac agagaagaac tagccatgtg ctatagggaa ccctgagtgc | 11400 |
| cctactcttt tcccaagaag ggtaaagcct acaatatcat caggggggcat gaagcacatt | 11460 |
| aatttgcagt ggctgcttca tatgaggaga tatggtggac aggctaattt ttccttgaaa | 11520 |
| atgtggcttc ttcaactcct ttcaaattta ggatggaata cttcctgaaa taaaactggg | 11580 |
| ctttatgcag gattctcttt gaaaattctt gtatgtccag aacaaaagat aaaactaatt | 11640 |
| gtattcctca cattcacaat ccccattggt ctgaagtcac gtagcacaga gcatctatag | 11700 |
| cacatagtgt ttaaagacta atgaatgcaa aaagataaaa tcttcaacta atttttgaat | 11760 |
| tgtttctcat atatgctact agaaaatgcc ttgttgatga agcacatttt gggtagttga | 11820 |
| ggtcttttgt tttcgccttt agcttttctaa gctttcttac aatgtggact gattactgta | 11880 |
| acatttcacg tgtaaaataa ctggatattc tttatatact ggaaataacc tgtgaatcca | 11940 |
| atatttcact aagtgtttta acttttgtgt atatatctct catcaataaa tgtggatttc | 12000 |
| aatttaaaaa aaaaaaaaaa a | 12021 |

<210> SEQ ID NO 4
<211> LENGTH: 1947
<212> TYPE: DNA
<213> ORGANISM: Mus musculus

<400> SEQUENCE: 4

| | |
|---|---|
| agccagtgca cttctacagc tgagagaatg gtcagtgcca acaatatgcc caagcaggta | 60 |
| gaagtgcgca tgcacgacag ccacctcagc tccgatgagc caaagcaccg aaacctgggc | 120 |
| atgcgcatgt gcgacaagct ggggaaaaat ctcctgctct cactgactgt gtttggtgtc | 180 |
| atcctgggag cagtgtgtgg cgggctgctt cgcttggcat cgcccatcca ccctgatgtg | 240 |
| gtcatgttga tagccttccc gggggacata ctcatgagga tgctgaagat gctcatcctc | 300 |
| cctcttatca tctccagttt aatcacaggg ttgtcaggcc tggatgctaa agccagcggc | 360 |
| cgcctaggca cgagagctat ggtgtattac atgtccacga ccatcattgc cgccgtgctg | 420 |
| ggggtcatcc tggtgttggc catccacccA ggcaatccca aactcaagaa gcagctaggg | 480 |
| cccgggaaga agaacgacga ggtgtctagc ctggatgcct tcctggatct cattagaaat | 540 |
| ctcttcccgg agaacctggt gcaagcctgt tccagcaga ttcagacagt gacaaagaaa | 600 |
| gttctggtgg cacctccatc tgaggaggcc aataccacca aggcggtcat ctccatgttg | 660 |
| aatgaaacca tgaacgaggc ccctgaagaa actaagatcg ttatcaagaa gggcctggag | 720 |
| ttcaaggacg ggatgaatgt cttaggtctg atcggattct ttattgcttt cggcattgcc | 780 |
| atggggaaga tgggtgaaca ggccaagctg atggtggagt tcttcaacat tctgaatgag | 840 |
| atcgtgatga agttagtgat catgatcatg tggtactccc ctctgggtat cgcctgcttg | 900 |
| atttgtggga agatcatcgc catcaaggac ttagaagtgg ttgctaggca gctggggatg | 960 |
| tacatgatca ccgtgatcgt gggcctcatc attcacgggg gcatctttct ccccttgatt | 1020 |
| tactttgtag tgaccagaaa aaatccattc tccttttttg ctggcatatt ccaagcctgg | 1080 |
| atcactgctc tgggaactgc ttccagtgct ggaactttgc ctgttacctt ccgttgcttg | 1140 |
| gaagataatc tagggattga caagcgtgtg accagattcg tcctcccagt cggagcaacc | 1200 |
| attaacatgg atggcacagc cctttacgag gctgtggcag ccattttcat agcccaaatg | 1260 |
| aatggggtca tcttggatgg aggtcagatt gtgactgtaa gccttacagc caccctggca | 1320 |
| agcattggtg cagccagtat tccaagcgcc gggctggtca ccatgctcct cattctcaca | 1380 |

-continued

```
gctgtgggcc tgccaacgga ggatatcagt ctgctggtgg cggtggactg gctgctggat    1440
agaatgagaa cttcagtcaa tgtggtgggc gattcttttg gggctgggat tgtctatcac    1500
ctttccaagt ctgagctgga caccattgac tcccaacacc gaatgcagga agacatcgaa    1560
atgaccaaga cgcagtccat ttacgacgac aagaaccaca gggaaagcaa ctctaatcag    1620
tgtgtctatg ccgcacacaa ctctgtcgta atagatgagt gcaaggtaac tctggcggcc    1680
aatgaaaagt cagctgactg cagtgttgag gaagaacctt ggaaacgtga aaataatga     1740 cccgattctc agccaattct tgaataaact ccccagcgta tcttatggta aagatgctc     1800 tctaaacagg cttcctttac aaaaggaaaa gatgcatatg tttctatgtt tacttaatct    1860
gttagctgag gcatagagga gctgtgtaca cccgtgatga taggcaccgt gctgtgtctt    1920
tgccaaataa tgctttatta actgtct                                        1947

<210> SEQ ID NO 5
<211> LENGTH: 20
<212> TYPE: DNA
<213> ORGANISM: Mus musculus

<400> SEQUENCE: 5
gaccaagacg cagtccattt                                                  20

<210> SEQ ID NO 6
<211> LENGTH: 20
<212> TYPE: DNA
<213> ORGANISM: Mus musculus

<400> SEQUENCE: 6
ggctgagaat cgggtcatta                                                  20

<210> SEQ ID NO 7
<211> LENGTH: 20
<212> TYPE: DNA
<213> ORGANISM: Mus musculus

<400> SEQUENCE: 7
gaccaagacg cagtccattt                                                  20

<210> SEQ ID NO 8
<211> LENGTH: 20
<212> TYPE: DNA
<213> ORGANISM: Mus musculus

<400> SEQUENCE: 8
gatgcaaggg gttgtgattt                                                  20

<210> SEQ ID NO 9
<211> LENGTH: 20
<212> TYPE: DNA
<213> ORGANISM: Mus musculus

<400> SEQUENCE: 9
atgttgaaat ggggaactcg                                                  20

<210> SEQ ID NO 10
<211> LENGTH: 20
<212> TYPE: DNA
<213> ORGANISM: Mus musculus

<400> SEQUENCE: 10
gccgttttcc aatcctatca                                                  20
```

```
<210> SEQ ID NO 11
<211> LENGTH: 20
<212> TYPE: DNA
<213> ORGANISM: Mus musculus

<400> SEQUENCE: 11
ggagcagatg gatgtttcgt                                              20

<210> SEQ ID NO 12
<211> LENGTH: 20
<212> TYPE: DNA
<213> ORGANISM: Mus musculus

<400> SEQUENCE: 12
gctaggagat ggctcctgtg                                              20

<210> SEQ ID NO 13
<211> LENGTH: 20
<212> TYPE: DNA
<213> ORGANISM: Homo sapiens

<400> SEQUENCE: 13
cttttggggc tgggatagtc                                              20

<210> SEQ ID NO 14
<211> LENGTH: 20
<212> TYPE: DNA
<213> ORGANISM: Homo sapiens

<400> SEQUENCE: 14
ttggctgcca gagttacctt                                              20
```

METHODS AND COMPOSITIONS FOR THE DIAGNOSIS AND TREATMENT OF DIABETES

This application is a U.S. national stage of PCT/EP2009/008256 filed on Nov. 20, 2009 which claims priority to and the benefit of U.S. Provisional Application No. 61/116,866 filed on Nov. 21, 2008, the contents of which are incorporated herein by reference.

The present invention relates to methods, assays and compositions for the diagnosis and treatment of diabetes. More particularly, the invention regards the use of glutamate transporters and/or receptors expressed in pancreatic islet cells as therapeutic tools or targets for the identification or treatment of individuals suffering from or susceptible to diabetes.

BACKGROUND OF THE INVENTION

The pathogenesis of both type 1 (T1DM) and type 2 diabetes mellitus (T2DM) is characterized by the gradual loss of insulin secreting pancreatic beta cells that precedes the onset of hyperglycemia. In T1DM beta cells are destroyed by an autoimmune process. Conversely, in T2DM is the combination of different stressful insults (insulin resistance with chronic insulin hypersecretion, low-grade chronic inflammation, redox stress and hyperglycemia itself) that, progressively, destroy the beta cells, with following hyperglucagonemia. During the preclinical stage, the remaining beta cells tend to compensate for ongoing beta cell loss by increasing insulin secretion and cell replication. These compensatory mechanisms maintain near-normoglycemia but do not arrest unremitting beta cell death. Ultimately, when residual beta cell mass is reduced to about 50% of the original, hyperglycemia occurs. Theoretically, the long preclinical phase present in both T1DM and T2DM, could allow therapeutic interventions aimed at promoting beta cell survival thereby preventing the development of overt diabetes.

The diagnosis of T1DM is commonly done in the presence of fasting hyperglycemia, a positive urine ketone test, and the detection of serological markers of diabetes autoimmunity. These are autoantibodies directed against the beta cell antigens insulin (IAA), glutamic acid decarboxylase (GAD) and insulinoma antigen 2 (IA-2). With the exclusion of insulin, none of these antigens is specific for the beta cell, being expressed also by other islet cell types (IA2) and GABAergic neurons (GAD). A proportion of patients shows autoantibodies directed against unknown cytoplasmic and membrane islet cell antigens (islet cell autoantibodies, ICA and islet cell surface autoantibodies, ICSA). Early reports showed that ICSA are cytotoxic for the beta cells but the actual existence of ICSA has been recently questioned. In subjects at risk of developing T1DM (first degree relatives of patients with T1DM) is the number and titre of the different autoantibodies that predict the development of the disease. Noteworthy, none of the autoantibodies described so far is pathogenic and they appear to be the results of "antigen spreading" consequent to beta death.

The diagnosis of T2DM is often occasional. T2DM patients are usually overweight, if not frankly obese, and insulin resistant. Insulin resistance induces beta cell hypersecretion and stimulates beta cell replication but, in genetically predisposed subjects, these compensatory mechanisms are destined to fail. In these subjects, chronic beta cell overstimulation, low-grade inflammation and redox stress (all features of the insulin resistant metabolic syndrome) progressively destroy the beta cells. Beta cell death is mediated by the accumulation of cytotoxic misfolded islet amyloid pancreatic polypeptide (IAPP) oligomers. Normally, IAPP is localized on the insulin granules and is co-secreted with insulin. Under stress conditions, IAPP processing by the endoplasmic reticulum become abnormal and misfolded cytotoxic IAPP oligomers accumulate in the cell.

In addition, replicating beta cells are even more susceptible than quiescent beta cells to misfolded IAPP oligomers so that the growth of new beta cells is severely impaired. Eventually, misfolded IAPP form fibrils that precipitates in the so called amyloid deposits which are the pathologic markers of T2DM but are present already before the onset of overt hyperglycemia.

T1DM treatment is based on the administration of exogenous insulin injections. Human recombinant or synthetic insulin analogs are injected before every meal and at bedtime to replace the lack of glucose-stimulated and basal endogenous insulin secretion. Insulin injections are cytoprotective since, by putting at rest the residual beta cells, can slow their functional exhaustion. Moreover, insulin administration restores near-normal glucose levels and reduces the deadly effect that chronic hyperglycemia "per se" exerts on the beta cells (so called glucose-toxicity).

Pharmacological treatment of T2DM is based on the administration of oral hypoglycaemic agents (OHAs) which are divided into insulin sensitizers (metformin and glytazones) and insulin secretagogues (sulphonylureas and glinides). Both class of OHAs are efficacious in restoring near-normoglycemia but none of them can arrest the progressive beta cell death. This is the reason why, over time, exogenous insulin administration is often required also in T2DM patients (so called secondary failure of OHAs). Recently, it has been suggested that insulin sensitizers, by probably reducing the metabolic demand and decreasing beta cell overstimulation, can increase their life span while sulphonylureas, by acting in the opposite way, can actually accelerate beta cell death and the secondary failure to OHAs.

Glutamate is the predominant excitatory neurotransmitter in the mammalian central nervous system (CNS) and is critical for essentially all physiological processes ranging from control of motor and somatosensory functions to information processing and storage. Recent studies highlight the presence of glutamate signal in peripheral tissues, and in particular in the endocrine pancreas (for a review see Skerry et al, 2001; Nedergaard et al, 2002; Hinoi et al, 2004).

At least five $Na^+$-dependent high affinity glutamate transporters (EAAT 1-5) have been identified. EAAC1/EAAT3 and EAAT4 are expressed in neuronal cells, GLT1/EAAT2 and GLAST/EAAT1 are restricted to glial cells, whereas EAAT5 is a retina specific glutamate transporter (for a review see Danbolt, 2001). Among these, GLT1 exhibits the highest level of expression and is responsible for most glutamate transport (Rothstein et al, 1996).

An high-affinity glutamate/aspartate transporter has been cloned from pancreas (Manfras et al, 1994), and pharmacological blockade of glutamate transporters with the non-selective TBOA inhibitor has been shown to modulate glucose-stimulated insulin secretion in pancreatic islets of (Weaver et al, 1998). However, it is not yet clear whether glutamate transporters are exclusively present in islet of Langherans, whether different isoforms are expressed in a cell specific-manner, as in the CNS, and their exact physiological relevance.

SUMMARY OF THE INVENTION

The invention is based on the unexpected finding that the glutamate transporter GLT1 is selectively expressed in pancreatic beta cells and that suppression of the transporter activity by pharmacological blockade or RNA interference is responsible for beta cells death, suggesting that a dysfunctional glutamate transport at the level of pancreatic cells or antibody-mediated blockage are involved in the pathogenesis of type 1 and type 2 diabetes mellitus (T1D or T2D). This finding is supported by the observations that autoantibodies against GLT1 are present in the serum of T1D patients and that intracellular GLT1 is detected in T2D patients, suggesting a direct role of the transporter in diabetes mellitus pathogenesis or progression.

According to a first embodiment, the invention is directed to a method for the diagnosis of diabetes in a subject, which comprises determining the presence of antibodies reactive to GLT1 in a biological fluid, preferably in a serum sample. Several assay formats can be used, in either liquid or solid phases, preferably through immuno-techniques in which the GLT1 transporter or an immunologically-active fragment thereof (e.g. an epitope-containing peptide) are contacted with a serum sample in conditions allowing the formation of an immune complex which is then detected by immunochemical or immunoenzymatic reactions. Alternatively, the presence of antibodies reactive to GLT1 in a biological fluid, preferably in a serum sample, is detected through a functional assay. A pancreatic cell line selected from beta TC3 or a cell line transfected with the GLT1 cDNA is incubated with a serum sample in conditions allowing the interaction of the antibodies with GLT1, and the modulating effects on GLT1 are determined through uptake experiments using a GLT1 radiolabelled substrate (glutamate or aspartate). The methods and assays according to the invention can be applied to the screening of individuals affected by diabetes or of subjects at risk of developing diabetes or LADA (Latent Autoimmune Diabetes in Adults).

In a further embodiment, the invention provides a method for the identification of compounds modulating the activity, expression or surface localization of GLT1, which comprises incubating the candidate compound with a pancreatic cell line selected from beta TC3 or a cell line transfected with the GLT1 cDNA and determining the GLT1-modulated effects through uptake, immunoprecipitation and western blotting and immunofluorescence experiments (described in materials and methods). Since GLT1 is endogenously expressed in beta-TC3, the latter can be used in cell-based assays for the screening of molecules having potential antidiabetic activity.

As discussed above, the autoimmune response against GLT1 transporter was found to be one of the pathogenic factors involved in diabetes onset/progression. Therefore it may be desirable to induce immunotolerance to GLT1 by administering the protein or an antigenic fragment thereof to a subject affected by or susceptible to diabetes. Thus, in a further embodiment, the invention provides the use of GLT1, an immunogenic fragment or derivative thereof, for the preparation of an immunotherapeutic composition for the treatment of diabetes.

According to a preferred embodiment of the invention, the GLT1 (mouse and rattus)/EAAT2(human) splice variant GLT1a, belonging to the SLC1a2 family (solute carrier family 1 (glial high affinity glutamate transporter), member 2) is the reference GLT1 protein for use in the applications herein provided. The human and mouse GLT1 amino acid sequences are identified in SEQ ID NO: 1 and 2, while the corresponding nucleotide sequences are identified in SEQ ID NO:3 and 4, respectively. The invention further includes variants and isoforms of such proteins, which maintain the functionality of glutamate transporter. For the uses herein envisaged, the structure and sequence of the GLT1 protein or peptides can be modified for such purposes as increasing purification, enhancing therapeutic or preventive efficacy, or stability (e.g. shelf life ex vivo and resistance to proteolytic degradation in vivo).

Compounds increasing GLT1 activity or preventing GLT1 inactivation, internalization or degradation, can be used to prevent beta cells death and develop a cyto-protective therapy. Accordingly, in another embodiment the invention regards the use of molecules positively modulating, particularly increasing the expression or function of GLT1 for the preparation of antidiabetic medicaments. Examples of such molecules include, but are not limited to, growth factors (Figiel M, Maucher T, Rozyczka J, Bayatti N, Engele J (2003) "Regulation of glial glutamate transporter expression by growth factors", Exp Neurol 183:124-135), neuroimmunophilin (Ganel R, Ho T, Maragakis N J, Jackson M, Steiner J P, Rothstein J D (2006) "Selective up-regulation of the glial Na-dependent glutamate transporter GLT1 by a neuroimmunophilin ligand results in neuroprotection", Neurobiol Dis 21:556-567), cAMP analogs or agents activating adenylate cyclase (Schlag B D, Vondrasek J R, Munir M, Kalandadze A, Zelenaia O A, Rothstein J D, Robinson MB (1998) "Regulation of the glial Na-dependent glutamate transporters by cyclic AMP analogs and neurons" Mol Pharmacol 53:355-369), thiazolidinic compounds whose mechanism of action involves the activation of GLT1 transcription, estrogens, neuronal secreted factor(s) including the pituitary adenylate cyclase activating peptide (Figiel M, Engele J (2000) "Pituitary adenylate cyclase-activating polypeptide (PACAP), a neuron-derived peptide regulating glial glutamate transport and metabolism" J Neurosci 20:3596-3605), beta-lactam antibiotics such as ceftriaxone (Rothstein J D, Patel S, Regan M R, Haenggeli C, Huang Y H, Bergles D E, Jin L, Dykes Hoberg M, Vidensky S, Chung D S, Toan S V, Bruijn L I, Su Z Z, Gupta P, Fisher P B (2005) "Beta-lactam antibiotics offer neuroprotection by increasing glutamate transporter expression"; Nature 433:73-77). Ceftriaxone, which is currently used in human therapy, is particularly preferred for increasing GLT1 expression in endocrine pancreas. The data indicate an action of Ceftriaxone also in a beta cell model, therefore also beta lactam-like compounds acting on GLT1 transcriptional activity, but lacking anti-microbial activity and non BBB permeant will provide an ideal tool for the prevention or treatment of diabetes mellitus.

Since the inhibition or suppression of the transporter activity causes the accumulation of extracellular glutamate which produces excitotoxic effects by sustained activation of glutamate receptors, inhibiting the ionotropic glutamate receptors, particularly AMPA and kainate receptors, will provide a valuable therapeutic strategy for protecting beta cells from glutamate toxicity. Accordingly, in a further embodiment, the invention relates to the use of glutamate receptor antagonists, preferably compounds able to inhibit or block AMPA and/or kainate ionotropic glutamate receptors, for the manufacture of medicaments for the prevention or treatment of diabetes.

The compounds modulating glutamate-transporter or glutamate-receptor function/activity can be administered separately or in combination; the amount of each compound will depend on the pharmaceutical form, administration route, potential interactions with other drugs, general conditions of the patient and on the severity of the disease. Generally, an effective amount will allow a partial or total recovery from the disease or the alleviation of its symptoms.

DETAILED DESCRIPTION OF THE INVENTION

Diagnostic Immuno Assay for Screening of DMT1 and LADA

The GLT1 protein is used in immunochemical assays to detect the presence of autoantibodies against the antigen in a serum sample and identify an individual at risk of developing diabetes. The GLT1 protein is incubated with the biological fluid to be tested under conditions which allow the antigen to complex with antibody in the fluid. The detection of complexes formed between the GLT1 protein or peptide and antibody is indicative of the presence of antibody against GLT1 protein in the serum sample.

Immunoprecipitation Assay

In this assay, GLT1 protein, recombinant or endogenously expressed in cells and tissues (brain), is incubated with the sample of biological fluid to be tested. The incubation is performed under conditions which allow the interaction between GLT1 protein and antibodies directed against the protein. The presence of complexes is revealed by immunoprecipitation with protein-A conjugated to beads and resolved by western blotting techniques using anti-GLT1 antibodies as a primary reagent and the appropriate secondary antibody. The detection of complexes formed between the GLT1 protein or peptide and antibody is indicative of the presence of antibody against GLT1 protein in the serum sample. The amount of label associated with the immunocomplex is compared to positive and negative controls to assess the presence or absence of anti-GLT1 antibody. In these assays, an immunoreactive form of the GLT1 protein, native, synthetic or recombinant forms of the whole molecule, or portions immunoreactive with an antibody against GLT1 may be used. In addition, modified GLT1 protein which has an amino acid sequence sufficiently duplicative of the GLT1 amino acid sequence so that they are immunoreactive with an autoantibody against GLT1 and provide an assay of suitable sensitivity and reliability can also be used. Beads formed of glass, polystyrene, polypropylene, dextran, agarose, sepharose, magnetic materials or other materials can be used to absorb protein-A.

Solid Phase Immunometric Assay

In this assay, purified GLT1 protein is immobilized on a solid phase support. The support is incubated with the sample of biological fluid to be tested. The incubation is performed under conditions which allow the interaction between immobilized GLT1 protein and antibodies directed against the protein. The solid phase support is then separated from the sample and a labeled anti-(human IgG) antibody is used to detect human anti-GLT1 antibody bound to the support. The amount of label associated with the support is compared to positive and negative controls to assess the presence or absence of anti-GLT1 antibody. In these assays, an immunoreactive form of the GLT1 protein or peptide are used. Native, synthetic or recombinant purified forms of the whole molecule, or portions immunoreactive with an antibody against GLT1 may be used. In addition, modified GLT1 protein which has an amino acid sequence sufficiently duplicative of the GLT1 amino acid sequence so that they are immunoreactive with an autoantibody against GLT1 and provide an assay of suitable sensitivity and reliability can also be used.

In the solid phase immunometric assay, purified GLT1 antigen can be adsorbed or chemically coupled to a solid phase support. Various solid phase supports can be used, such as beads formed of glass, polystyrene, polypropylene, dextran or other material. Other suitable solid phase supports include tubes or plates formed from or coated with these materials. The GLT1 protein can be either covalently or non-covalently bound to the solid phase support by techniques such as covalent bonding via an amide or ester linkage or adsorption.

The support containing GLT1 protein, functions to selectively insolubilize antibody in the liquid sample tested. In a blood test for anti-GLT1 antibody, the support is incubated with blood plasma or serum. Before incubation, plasma or serum can be diluted with normal animal plasma or serum. The diluent plasma or serum is derived from the same animal species that is the source of the anti-(human IgG) antibody. The preferred anti-(human IgG) antibody is goat anti-(human IgG) antibody. Thus, in the preferred format, the diluent would be goat serum or plasma. The conditions of incubation, e.g., pH and temperature, and the duration of incubation are not crucial. These parameters can be optimized by routine experimentation. Generally, the incubation will be run for 1-2 hours at about 4° C. in a buffer of pH 7-8.

After incubation, the solid phase support and the sample are separated by any conventional technique such as sedimentation or centrifugation. The solid phase support then may be washed free of sample to eliminate any interfering substances.

To assess human antibody bound to the solid phase support, a labeled anti-(human IgG) antibody (tracer) is used. Generally, the solid phase support is incubated with a solution of the labeled anti-(human IgG) antibody which contains a small amount (about 1%) of the serum or plasma of the animal species which serves as the source of the anti-(human IgG) antibody. Anti-(human IgG) antibody can be obtained from any animal source. However, goat anti-(human IgG) antibody is preferred. The anti-(human IgG) antibody can be an antibody against the $F_c$ fragment of human IgG, for example, goat anti-(human IgG) $F_c$ antibody.

The anti-(human IgG) antibody can be labeled with a radioactive material such as $^{125}$Iodine, with an optical label, such as a fluorescent material, or with an enzyme such as horseradish peroxidase. The antihuman antibody can also be biotinylated and labeled avidin used to detect its binding to the solid phase support.

After incubation with the labeled antibody, the solid phase support is separated from the solution and the amount of label associated with the support is evaluated. The label may be detected by a gamma counter if the label is a radioactive gamma emitter, or by a fluorimeter, if the label is a fluorescent material. In the case of an enzyme, the label may be detected calorimetrically employing a substrate for the enzyme.

The amount of label associated with the support is compared with positive and negative controls in order to determine the presence of anti-GLT1 antibody. The controls are generally run concomitantly with the sample to be tested. A positive control is a serum containing antibody against the GLT1 protein; a negative control is a serum from individuals (e.g., non-prediabetic individuals) which does not contain antibody against the GLT1 protein.

Diagnostic Functional Assay for Screening of DMT1 and LADA

In this assay, a pancreatic cell line selected from beta TC3 or a cell line transfected with wild type or recombinant GLT1 cDNA is incubated with the sample of biological fluid to be tested. The conditions of incubation, e.g., pH and temperature, and the duration of incubation can be optimized by routine experimentation. In a blood test for anti-GLT1 antibody, generally cells are incubated with blood plasma or serum for 2-3 hours at 37° C. Before incubation, plasma or serum is diluted at 20%.

The interaction of the antibodies with GLT1 is determined through uptake experiments using a GLT1 radioactive substrate (glutamate or aspartate).

The modulation (up or down regulation) of uptake values is indicative of the presence of antibodies against GLT1 protein in the serum sample. The uptake values obtained in the presence of serum samples are corrected for the non-GLT1-mediated glutamate/aspartate uptake and compared to controls to assess the presence or absence of anti-GLT1 antibodies. The controls are uptake values obtained with non pre-diabetic or non diabetic subjects. The non-GLT1-mediated glutamate/aspartate uptake is calculated performing uptake experiments in the presence of 0.3 mM DHK. This method could be useful for routine T1D diagnosis, and presents several advantages: it is sensitive, specific and the results are quantitative and suitable for serial estimations. The assay, performed in 96-well plates, can be automated, allowing high-throughput screening, and resulting in materials, samples and time saving procedures; therefore the costs and the experimental variability can be reduced. It doesn't require any particular radioisotope, so less dangerous radioisotopes can be used for the aminoacid labelling.

Modification of GLT1 Molecule

A modified GLT1 protein or modified peptide can be produced in which the amino acid sequence has been altered, such as by amino acid substitution, deletion, or addition, to modify immunogenicity and/or increase therapeutic effectiveness or to which a component has been added for the same purpose. For example, additional amino acid residues derived from the GLT1 sequence or other sequence can be attached to either the amino terminus, the carboxy terminus, or both the amino terminus and carboxy terminus of the GLT1 protein. Non-GLT1 derived sequences include residues which may increase solubility or facilitate purification, such as a sequence attached to the GLT1 protein to aid purification of protein produced by recombinant technique (STREP-TAG). Site-directed mutagenesis of DNA encoding the GLT1 protein or a peptide thereof can be used to modify the structure of the GLT1 protein or peptide. Such methods may involve PCR (Ho et al., Gene, 77:51-59 (1989)) or total synthesis of mutated genes (Hostomsky, Z., et al., Biochem. Biophys. Res. Comm., 161:1056-1063 (1989)).

Antigenic fragments or peptides derived from the GLT1 protein are within the scope of the invention. Fragments within the scope of the invention include those which induce an immune response in mammals, preferably humans, such as the production of IgG and IgM antibodies or elicit a T-cell response such as T-cell proliferation and/or lymphokine secretion and/or the induction of T-cell anergy. Fragments of the nucleic acid sequence coding for the GLT1 protein are also within the scope of the invention. As used herein, a fragment of a nucleic acid sequence coding for the GLT1 protein refers to a nucleotide sequence having fewer bases than the nucleotide sequence coding for the entire amino acid sequence of the GLT1 protein. Nucleic acid sequences used in any embodiment of this invention can be cDNA as described herein, or alternatively, can be any oligodeoxynucleotide sequence having all or a portion of a sequence represented herein, or their functional equivalents. Such oligodeoxynucleotide sequences can be produced chemically or automatically using known techniques.

Given the nucleic acid sequence and deduced amino acid sequence of the GLT1 protein, it is possible to identify peptides which contain T- or B-cell epitopes. An epitope is the basic element or smallest unit of recognition by a receptor where the epitope comprises amino acid residues essential to receptor recognition. For example, peptides containing T cell epitopes associated with interaction with the T-cell receptor (TCR) on helper T-cells can be identified. These T cell epitopes are usually at least 7 amino acid residues in length and, when associated with the MHC II glycoprotein present on the surface of antigen-presenting cells, form a complex that interacts with the TCR. Relevant peptides comprising at least one T cell epitope of the PM-1 protein can be identified by dividing the GLT1 protein into overlapping or non-overlapping peptides of desired lengths, which may be produced recombinantly or synthetically. The peptides can be cultured in the presence of antigen-presenting cells in a standard T-cell proliferation assay to determine the ability of the peptide to stimulate T-cell proliferation as indicated by, for example, cellular uptake of labeled thymidine. Peptides derived from the GLT1 protein with altered structures can be designed which retain their ability to complex with MHC II glycoprotein but fail to effect reaction with TCR by assessing the ability of these altered peptides to inhibit the T-cell proliferation in the presence of known activators in this assay.

Immunological Therapy

The GLT1 protein can be employed in novel therapeutic methods to treat an autoimmune disease in an individual. The GLT1 protein, or antigenic fragment thereof, can be administered to a diabetic or prediabetic individual to prevent the progression or development of Type I diabetes in the individual. The GLT1 protein, or at least one antigenic fragment, in the form of a therapeutic composition, is administered simultaneously or sequentially to the individual in an amount effective to prevent the progression or development of diabetes in the individual. In addition, the therapeutic composition can be administered under non-immunogenic conditions to tolerize the individual to the GLT1 protein, rather than elicit an immune response. As used herein, tolerization is defined as non-responsiveness or diminution in symptoms upon exposure to the GLT1 protein. Techniques for administration of tolerizing doses of antigens are known in the art, including administration of the GLT1 protein, or fragment thereof, in the absence of adjuvant and/or in soluble form. Administration of a peptide derived from the GLT1 protein comprising at least one T cell epitope may tolerize appropriate T cell subpopulations such that they become unresponsive to the GLT1 protein. Therapeutic methods that utilize antagonist peptides of the GLT1 protein which bind the MHC II glycoprotein but result in a complex which is not interactive with the TCR can also be used.

The GLT1 protein or peptide thereof may be administered alone or in concert with anti-CD4 antibodies or other CD4 blockers. This approach to conferring tolerance is disclosed in U.S. Pat. Nos. 4,681,760 and 4,904,481. In this approach, the antigen and the anti-CD4 antibodies or immunoreactive fragments are administered concomitantly. By "concomitant" administration is meant within a time frame which permits the anti-CD4 component to block the helper T-cell response to the antigen. The nature of "concomitant" in this sense is described in the above-referenced U.S. patents, incorporated herein by reference.

The GLT1 protein or fragment thereof is combined with a pharmaceutically acceptable carrier or diluent to form a therapeutic composition. Pharmaceutically acceptable carriers include polyethylene glycol (Wie et al. International Archives of Allergy and Applied Immunology 64:84-99 (1981)) and liposomes (Strejan et al. Journal of Neuroimmunology 7:27 (1984)). Pharmaceutically acceptable diluents include saline and aqueous buffer solutions. Such compositions will generally be administered by injection subcutaneously, intravenously or intraperitoneally, oral administration, (e.g., as in the form of a capsule) inhalation, transdermal application or rectal administration.

Pharmacological Therapy

Although T1M and T2M are caused by different mechanisms, both types are characterized by a pronounced reduction in beta-cell mass (more than 50%), in late stages. As decreases in cell mass can take several years to develop, a cyto-protective therapy may be useful for both types of diabetes. At least two different targets have been identified:

1. Ionotropic glutamate receptors (AMPA, kainate): data from FIG. 1C indicate that the pharmacological inhibition of AMPA, kainate receptors protects beta cells from glutamate toxicity. According to the invention, the following antagonists can be used for the treatment or prevention of diabetes or LADA.

AMPA/Kainate Selective: Antagonists 1) 4-(8-Methyl-9H-1,3-dioxolo[4,5-h][2,3]benzodiazepin-5-yl)-benzenamine hydrochloride References: Tarnawa et al (1989) Electrophysiological studies with a 2,3-benzodiazepine muscle relaxant: GYKI 52466. Eur. J. Pharmacol. 167 193. Donevan and Rogawski (1993) GYKI 52466, a 2,3-benzodiazepine, is a highly selective, non-competitive antagonist of AMPA/kainate receptor responses. Neuron 10 51. Paternain et al (1995) Selective antagonism of AMPA receptors unmasks kainate receptor-mediated responses in hippocampal neurons. Neuron 14 185. Rzeski et al (2001) Glutamate antagonists limit tumor growth. Proc. Natl. Acad. Sci. USA 98 6372. Szabados et al (2001) Comparison of anticonvulsive and acute neuroprotective activity of three 2,3-benzodiazepine compounds, GYKI 52466, GYKI 53405, and GYKI 53655. Brain Res. Bull. 55 387.

2) 6-Cyano-7-nitroquinoxaline-2,3-dione 3) 6-Cyano-7-nitroquinoxaline-2,3-dione disodium References: Honore et al (1988) Quinoxalinediones: potent competitive non-NMDA glutamate receptor antagonists. Science 241 701. Watkins et al (1990) Structure-activity relationships in the development of excitatory amino acid receptor agonists and competitive antagonists. TiPS 11 25. Long et al (1990) Effect of 6-cyano-2,3-dihydroxy-7-nitro-quinoxaline (CNQX) on dorsal root-, NMDA-, kainate and quisqualate-mediated depolarization of rat motoneurones in vitro. Br. J. Pharmacol. 100 850. King et al (1992) Antagonism of synaptic potentials in ventral horn neurones by 6-cyano-7-nitroquinoxaline-2,3-dione: a study in the rat spinal cord in vitro. Br. J. Pharmacol. 107 375.

4) 6,7-Dinitroquinoxaline-2,3-dione

References: Honore et al (1988) Quinoxalinediones: potent competitive non-NMDA glutamate receptor antagonists. Science 241 701. Watkins et al (1990) Structure-activity relationships in the development of excitatory amino acid receptor agonists and competitive antagonists. TiPS 11 25.

5) 2,3-Dioxo-6-nitro-1,2,3,4-tetrahydrobenzo[f]quinoxaline-7-sulfonamide

References: Gill et al (1992) The neuroprotective actions of 2,3-dihydroxy-6-nitro-7-sulfamoylbenzo(f)quinoxaline (NBQX) in a rat focal ischaemia model. Brain Res. 580 35. Zeman and Lodge (1992) Pharmacological characterization of non-NMDA subtypes of glutamate receptors in the neonatal rat hemisected spinal cord in vitro. Br. J. Pharmacol. 106 367. Sheardown et al (1993) The pharmacology of AMPA receptors and their antagonists. Stroke 24 Suppl 1 146. Namba et al (1994) Antiepileptogenic and anticonvulsant effects of NBQX, a selective AMPA receptor antagonist, in the rat kindling model of epilepsy. Brain Res. 638 36.

6) 2,3-Dioxo-6-nitro-1,2,3,4-tetrahydrobenzo[f]quinoxaline-7-sulfonamide disodium salt References: Gill et al (1992) The neuroprotective actions of 2,3-dihydroxy-6-nitro-7-sulfamoylbenzo(f)quinoxaline (NBQX) in a rat focal ischaemia model. Brain Res. 580 35. Zeman and Lodge (1992) Pharmacological characterization of non-NMDA subtypes of glutamate receptors in the neonatal rat hemisected spinal cord in vitro. Br. J. Pharmacol. 106 367. Sheardown et al (1993) The pharmacology of AMPA receptors and their antagonists. Stroke 24 Suppl 1 146. Namba et al (1994) Antiepileptogenic and anticonvulsant effects of NBQX, a selective AMPA receptor antagonist, in the rat kindling model of epilepsy. Brain Res. 638 36.

7) 6,6-[(3,3'-Dimethyl[1,1'-biphenyl]-4,4'-diyl)bis(azo)bis[4-amino-5-hydroxy-1,3-naphthalenedisulphonic acid]tetrasodium salt References: Merck Index 12 3952. Roseth et al (1995) Uptake of L-glutamate into rat brain synaptic vesicles: effect of inhibitors that bind specifically to the glutamate transporter. J. Neurochem. 65 96. Whittenburg et al (1996) $P_2$-purinoceptor antagonists: II blockade of P2-purinoceptor subtypes and ecto-nuleotidase by compounds related to Evans blue and trypan blue. Naunyn-Schmied. Arch. Pharmacol. 354 491. Price and Raymond (1996) Evans blue antagonizes both α-amino-3-hydroxy-5-methyl-4-isoxazolepropionate and kainate receptors and modulates desensitization. Mol. Pharmacol. 50 1665. Schurmann et al (1997) Differential modulation of AMPA receptor mediated currents by Evans Blue in postnatal rat hippocampal neurones. TiPS 121 237.

8) (±)-4-(4-Aminophenyl)-1,2-dihydro-1-methyl-2-propylcarb amoyl-6,7-methylenedioxyphthalazine References: Li et al (1996) Kainate-receptor-mediated sensory synaptic transmission in mammalian spinal cord. Nature 397 161. Pelletier et al (1996) Substituted 1,2-dihydrophthalazines: potent, selective and non-competitive inhibitors of the AMPA receptor. J. Med. Chem. 39 343. Bleakman et al (2002) Kainate receptor agonists, antagonists and allosteric modulators. Curr. Pharm. Des. 8 873.

9) (aS)-a-Amino-3-[(4-carboxyphenyl)methyl]-3,4-dihydro-2,4-dioxo-1(2H)-pyrimidinepropanoic acid References: More et al (2002) The novel antagonist 3-CBW discriminates between kainate receptors expressed on neonatal rat motoneurones and those on dorsal root C-fibres. Br. J. Pharmacol. 137 1125. More et al (2003) Structural requirements for novel willardiine derivatives acting as AMPA and kainate receptor antagonists. Br. J. Pharmacol. 138 1093.

10) [[3,4-Dihydro-7-(4-morpholinyl)-2,3-dioxo-6-(trifluorom ethyl)-1(2H)-quinoxalinyl]methyl]phosphonic acid References: Turski et al (1998) ZK200775: a phosphonate quinoxalinedione AMPA antagonist for neuroprotection in stroke and trauma. Proc. Natl. Acad. Sci. USA. 95 10960. Kosowski et al (2004) Nicotine-induced dopamine release in the nucleus accumbens is inhibited by the novel AMPA antagonist ZK200775 and the NMDA antagonist CGP39551. Pychopharmacology 175 114. Elger et al (2005) Novel α-amino-3-hydroxy-5-methyl-4-isoxazole propionate (AMPA) receptor antagonists of 2,3-benzodiazepine type: chemical synthesis, in vitro characterization, and in vivo prevention of acute neurodegeneration. J. Med. Chem. 48 4618.

AMPA/Kainate Selective: Desensitization Modulators 11) 2-[2,6-Difluoro-4-[[2-[(phenylsulfonyl)amino] ethyl]thio]phenoxy]acetamide References: Sekiguchi et al (1997) A novel allosteric potentiator of AMPA receptors: 4-[2-(phenylsulfonylamino) ethylthio]-2,6-difluoro-phenoxyacetamide. J. Neurosci. 17 5760. Sekiguchi et al (2001) The AMPA receptor allosteric potentiator PEPA ameliorates post-ischemic memory impairment. Neuroreport 12 2974. Sekiguchi et al (2002) A desensitization-selective potentiator of AMPA-type glutamate receptors. Br. J. Pharmacol. 136 1033.

AMPA/Kainate Selective: Miscellaneous 12) (R)-a-Amino-3-hydroxy-5-methyl-4-isoxazolepropionic acid References: Hansen et al (1983) Enzymic resolution and binding to rat brain membranes of the glutamic acid agonist α-amino-3-hydroxy-5-methyl-4-isoxazolepropionic acid. J. Med. Chem. 26 901. Lauridsen et al (1985) Ibotenic acid analogues. Synthesis, molecular flexibility, and in vitro activity of agonists and antagonists at central glutamic acid receptors. J. Med. Chem. 28 668.

AMPA Selective: Antagonist 13) 1-(4'-Aminophenyl)-3,5-dihydro-7,8-dimethoxy-4H-2,3-ben zodiazepin-4-one References: Chimirri et al (1997) 1-Aryl-3,5-dihydro-4H-2,3-benzodiazepin-4-ones: novel AMPA receptor antagonists. J. Med. Chem. 40 1258. De Sarro et al (1999) Effects of some AMPA receptor antagonists on the development of tolerance in epilepsy-prone rats and in pentylenetetrazole kindled rats. Eur. J. Pharmacol. 368 149. De Sarro et al (1999) Anticonvulsant activity and plasma level of 2,3-benzodiazepin-4-ones (CFMs) in genetically epilepsy-prone rats. Pharmacol. Biochem. Behav. 63 621.

14) N,N,N,-Trimethyl-5-[(tricyclo[3.3.1.13,7]dec-1-ylmethyl)amino]-1-pentanaminiumbromide hydrobromide References: Magazanik et al (1997) Block of open channels of recombinant AMPA receptors and native AMPA/kainate receptors by adamantane derivatives. J. Physiol. 505 655. Buldakova et al (1999) Characterization of AMPA receptor populations in rat brain cells by the use of subunit-specific open channel blocking drug, IEM-1460. Brain Res. 846 52. Schlesinger et al (2005) Two mechanisms of action of the adamantane derivative IEM-1460 at human AMPA-type glutamate receptors. Br. J. Pharmacol. 145 656.

15) (S)—N-[7-[(4-Aminobutyl)amino]heptyl]-4-hydroxy-a-[(1-oxobutyl)amino]benzenepropanamide dihydrochloride References: Nilsen and England (2007) A subtype-selective, use-dependent inhibitor of native AMPA receptors. J. Am. Chem. Soc. 129 4902.

16) 1,4-Dihydro-6-(1H-imidazol-1-yl)-7-nitro-2,3-quinoxalin edione hydrochloride References: Ohmori et al (1994) 6-(1H-imidazol-1-yl)-7-nitro-2,3(1H,4H)-quinoxalinedione hydrochloride (YM90K) and related compounds: structure-activity relationships for the AMPA-type non-NMDA receptor. J. Med. Chem. 37 467. Umemura et al (1997) Neuroprotective effect of a novel AMPA receptor antagonist, YM90K, in rat focal cerebral ischaemia. Brain Res. 773 61. Nakano et al (2001) A potent AMPA/kainate receptor antagonist, YM90K, attenuates the loss of N-acetylaspartate in the hippocampal CA1 area after transient unilateral forebrain ischemia in gerbils. Life Sci. 69 1983.

Miscellaneous Glutamate:

17) g-D-Glutamylglycine

References: Jones et al (1984). Structure-activity relations of dipeptide antagonists of excitatory amino acids. Neuroscience 13 537. Aksenov et al (2005) Glutamate neurotransmission in the cerebellar interposed nuclei: involvement in classical conditioned eyeblinks and neuronal activity. J. Neurophysiol. 93 44.

2. Glutamate transporter GLT1: as a further strategy to prevent beta-cell death in diabetic patient according to the present invention, GLT1 expression or localization or function is increased by means of:

drugs known to induce GLT1 expression: growth factors (BDNF, PDGF, FGF, CNGF, IGF); neuroimmunophilin; cAMP analogs or agents activating adenylate cyclase (PACAP, also expressed in pancreas); thiazolidinic compounds, whose mechanism of action involves the activation of GLT1 transcription; estrogen; b-lactam antibiotics such as ceftriaxone drugs known to prevent GLT1 inactivation/internalization/degradation: anti-oxidants, in particular compounds against ros (reactive oxygen species)

drugs known to increase GLT1 function: riluzole; nordhydroguaiaretic acid (Boston-Howes et al, (2008) Nordhydroguaiaretic acid increases glutamate uptake in vitro and in vivo: therapeutic implications for amyotrophic lateral sclerosis. Exp. Neurol. 213, 229) drugs acting on group I or group III metabotropic receptors (agonist or antagonist).

Figure 1A:
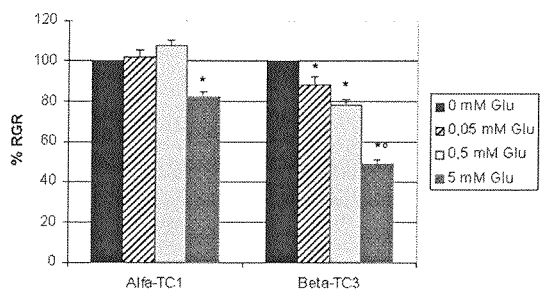
FIG. 1: CHRONIC GLUTAMATE INCUBATION CAUSES SELECTIVE B-CELL DEATH WHICH IS MEDIATED BY IONOTROPIC CHANNEL OVERACTIVATION.

1A: Glutamate induces a dose-dependent beta-cell death. 24 hrs after plating, αTC1 and βTC3 cells were incubated for five days with the indicated glutamate concentrations and viability was assessed by MTT assay. Data are presented as % Relative Growth Rate (RGR) versus controls (100%) and represent the mean±SE of at least 7 independent experiments (n=6). * $p<0.01$ vs ctrl; ° $p<0.01$ vs Glu 5 mM in αTC1.

1B: Glutamate overstimulation causes increased β-cell apoptosis. 24 hours after plating, βTC3 cells were incubated for five days with 0.5 mM glutamate, and cell apoptosis was assessed by TUNEL assay. The cell nuclei were labelled with PrI. Histograms on the right represent TUNEL positive cells per field, and are the mean±SE of two independent experiments performed in duplicate.

1C: β-cell death is prevented by pharmacological inhibition of ionotropic channels. 24 hrs after plating, αTC1 and βTC3 cells were incubated for five days with 0.025 mM CNQX (left panel) or 0.1 mM APV (right panel), in the presence or the absence of 5 mM glutamate and viability was assessed by MTT assay. Data are presented as % RGR versus control samples (100%) and represent the mean±SE of three independent experiments (n=5). * p<0.05

FIG. 2: EXPRESSION OF HIGH-AFFINITY GLUTAMATE TRANSPORTER IN αTC1 AND βTC3

2A. PCR analysis of glutamate transporter types. Total RNA was extracted from βTC3 and αTC1 cells, and RT-PCR was performed with primers specific for the different glutamate transporter types (T) (GLAST, GLT1A, GLT1B and EAAC1) and for tubulin. As a negative control (NT) RT-PCR was performed in the absence of M-MLU reverse transcriptase. Left: DNA Marker.

2B: Immunoblotting of αTC1 and βTC3 lysates with specific anti-glutamate transporters antibodies. 20 µg of brain P2 fraction or 20 µg of βTC3 or αTC1 whole lysate extracts were separated onto a 9% SDS-PAGE and the expression of glutamate transporter was detected using specific anti-glutamate transporter antibodies or a pre-immune serum. **oligomer; *monomer 2C: GLT1 immunostaining. βTC3 cells were fixed in methanol and immunostained with an anti-GLT1 antibody followed by a FITC-conjugated anti rabbit IgG. bar=5 µm 2D: 3H-D-Aspartate uptake. Four days after plating the Na-dependent (NaCl) and Na-independent (ChCl) [3H]-D-Aspartate uptake was measured in αTC1 and βTC3 cells. Data are expressed as cpm/well/10 min and represent the mean±SE of at least three independent experiments performed in triplicate. * (NaCl vs ChCl) P<0.001; ° (DHK versus control) P<0.001.

FIG. 3: GLT1A EXPRESSION IN ISOLATED HUMAN ISLETS

3A: PCR analysis of GLT1 expression in human islets. Total RNA was extracted from 1000 human isolated islets, and RT-PCR was performed with primers specific for the GLT1A and tubulin. As a negative control (C), RT-PCR reaction was performed in the absence of cDNA template. Left: DNA Marker (M).

3B: 3H-D Aspartate uptake. The Na-dependent (NaCl) and Na-independent (ChCl) [3H]-D-Aspartate uptake was measured in 40, hand picked, isolated human islets. To determine GLT1-mediated aspartate uptake, 0.3 mM DHK was added to the uptake solution. Data are expressed as % of Na-dependent uptake (NaCl) and represent the mean±SE of at least three independent experiments performed in triplicate. * (DHK versus controls) P<0.001.

3C: Immunoprecipitation of GLT1 from brain and islet lysates. 1000 human islets were lysed and 100 µg of whole lysate extract or P2 brain fraction was immunoprecipitated with the anti-GLT1 antibody or a rabbit serum. Immunoprecipitated were separated onto 9% SDS-PAGE and immunoblotted with specific anti-GLT1 antibody. 50-100 µg of P2 brain fraction or islet extract was loaded in the same gel (Tot). **oligomer; *monomer; ° a specific band.

FIG. 4. GLT1 IMMUNOLOCALIZATION IN HUMAN PANCREAS SECTIONS

4A: Immunohystochemical analysis. Himmunohystochemistry (HRP staining) of paraffin embedded human pancreas sections with a selective anti-GLT1 antibody. 40× (left) and 100× (right) image magnifications are shown.

4B. Double immunofluorescence analysis: paraffin embedded human pancreas sections were double immunostained with anti-GLT1 and hormones as markers of different endocrine cell types, as indicated. Bar=10 µm. In the inset, a particular of the islet is shown at higher magnification (2×).

Figure 5:
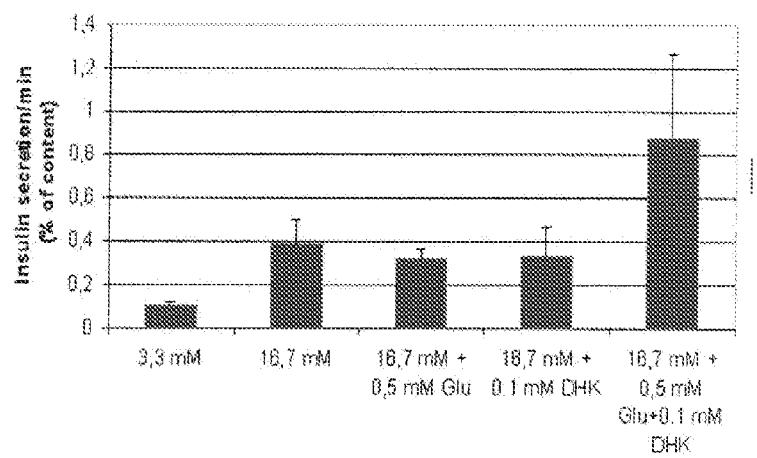

FIG. 5: GLT1 CONTROLS HORMONE SECRETION IN HUMAN ISOLATED ISLETS. 48 hours after isolation, 20 human islets per tube were exposed to 3.3 or 16.7 mM glucose in the absence and the presence of either L-glutamate (0.5 mM), DHK (0.3 mM) or both L-glutamate and DHK, and insulin secretion measured. Levels of secreted insulin from islets were normalized to total insulin content. Data are expressed as % of insulin content and represent the mean±SD of two independent experiments performer in duplicate.

FIG. 6. PHARMACOLOGICAL INHIBITION OF THE GLUTAMATE TRANSPORTER GLT1 INDUCES β-CELL DEATH

6A: Dose-Dependent Inhibition of 3H-D-Aspartate Uptake by DHK $3 \times 10^5$ βTC3 cells/well were plated onto 24-well culture plates and the Na-dependent [3H]-D-Aspartate uptake was measured in the presence or the absence of increasing DHK concentrations (0.05-0.3 mM). Data are expressed as cpm/well/10 min and represent the mean±SE of at least three independent experiments performer in triplicate. * (DHK versus controls) P<0.001.

6B. MTT assay. 24 hrs after plating, αTC1 and βTC3 cells were incubated for five days with different DHK concentrations and viability was assessed by MTT assay. Data are presented as % RGR versus control (100%) and represent the mean±SE of three independent experiments (n=8). * (DHK versus control) p<0.05

6C TUNEL assay: 24 hours after plating, βTC3 cells were incubated for five days with 0.1 mM DHK, and cell apoptosis was assessed by TUNEL assay. Cell nuclei were labelled with PrI. Data are presented as TUNEL positive cells per field (histograms on the right), and are the mean±SE of two independent experiments performed in duplicate. * P<0.05

6D ShRNA interference. βTC3 cells were transfected with two different shRNA directed against GLT1 (Sh1, Sh3) or a control shRNA (ShC), and three days after transfection, cells were assayed for 3[H]-D-aspartate uptake (b) or lysed and the presence of GLT assayed by western blotting (a) or fixed and processed for TUNEL (c).

FIG. 7 DOWN REGULATION OF THE GLUTAMATE TRANSPORTER GLT1/EAAT2 INDUCES β-CELL DEATH IN HUMAN ISOLATED ISLETS.

7A: MTT assay: 48 hrs after isolation, 20 islets/tube were incubated for three days with the indicated glutamate and DHK concentrations in the presence of 3.3 mM glucose or 16.7 mM glucose and viability was assessed by MTT assay. Data are expressed as % Relative Growth Rate (% RGR) versus control samples and are the means±SE of three different experiments performed in triplicate.

7B: TUNEL assay: 48 hrs after isolation, islets were incubated for three days with 0.5 mM glutamate (GLU), 0.1 mM DHK (DHK) or both (GLU+DHK) in the presence of 11 mM glucose and cell apoptosis was assessed by TUNEL assay. To label β-cells, isltes were double stained with insulin.

FIG. 8 PHARMACOLOGICAL UP-REGULATION OF THE GLUTAMATE TRANSPORTER GLT1/EAAT2 RESTORES B-CELL VIABILITY.

8A: GL1 expression. 150.000 cells were plated on 3.5 mm diameter Petri dishes and 24 hours after plating, they were incubated with 10 µM ceftriaxone for five days. After incubation cells were lysed and 100 µg of whole lysate extracts were separated onto a 9% SDS-PAGE and the expression of glutamate transporter was detected using specific anti-GLT1 or anti-β-catenin antibodies. The expression of GLT1 was quantified by densitometry, and normalized over β-catenin content. Shown is a representative experiment; Similar results were obtained in two other independent experiments.

8B: MTT assay: 24 hrs after plating, βTC3 cells were incubated for five days with the indicated ceftriaxone concentrations in the presence or absence of 5 mM glutamate and viability was assayed by MTT assay. Data are presented as % RGR versus control (100%) and represent the mean±SE of three independent experiments (n=8). *(ceftriaxone versus relative control) p<0.05.

FIG. 9. AUTOANTIBODIES AGAINST GLT1 ARE PRESENT IN DMT1 PATIENT SERUM SAMPLES

9A: Immunoprecipitation of GLT1 with serum samples of DMT1 patients. COS cells were transfected with mouseGLT1 cDNA. 48 hours after transfection, cells were lysed and 100 μg of whole cell extract was immunoprecipitated with anti-GLT1 antibody, control serum from healthy subject (C6) or three different serum samples from T1D patients (D1, D2, D6). Immunoprecipitates were separated by SDS-PAGE and immunoblotted with the anti-GLT1 antibody. As a negative control, 100 μg of whole lysate from mock-transfected COS cells was immunoprecipitated in the same conditions.

9B: GLT1 immunoprecipitation from mouse brain with serum samples of DMT1 patients. 50-100 μg of P2 brain fractions were immunoprecipitated with the anti-GLT1 antibody or five different sera from healthy subjects (C1-C5) or T1D patients (D1-D5). GLT1 immunoprecipitates were separated by SDS-PAGE and revealed by immunoblotting with the anti-GLT1 antibody.

To determine the level of GLT1 autoreactivity, the 60 KDa band was quantified by densitometry. Data are presented as fold over mean control.

9C: Immunostaining of GLT1 and EAAC1 transfected cells with control and T1D serum samples. COS cells were transfected with mouseGLT1 or ratEAAC1 cDNAs, as indicated, and 48 hours after transfection, they were fixed in methanol and immunostained with an anti-GLT1 antibody, a control serum (C1) or three different serum samples from T1D patients (D1, D2 and D4). Bar: 10 μm.

9D: Modulation of [3H]-D aspartate uptake by incubation with serum samples from DMT1 patients. βTC3 cells were plated onto 96-wells culture plates and the Na-dependent [3H]-D-Aspartate uptake was measured after cells pre-incubation with 20% serum samples for three hours at 37° C. Data are expressed as a percentage of mean uptake values in control subjects. Sera from 12 control subjects and 23 T1D patients were tested and reported as single point on the graph. Each point is the mean of at least two independent uptake experiments performed in triplicate. Activating or inhibiting sera are considered samples with an uptake value more then 2SD above or below the mean of controls subjects, respectively. In the insert are representative GLT1 immunoprecipitation experiments obtained with sera of the related categories.

FIG. 10: IMMUNOLOCALIZATION OF GLT1 IN HUMAN PANCREAS SECTIONS OF T2D PATIENTS

Human pancreas from 6 healthy controls (upper panels) or 7 T2D patients (lower panels) were immunostained with the anti-GLT1 antibody followed by HRP-conjugated anti-rabbit IgG. Images magnification was 40× (left panels) and 100× (right panels).

EXPERIMENTAL

Materials and Methods
Cell Lines

βTC3 and αTC1 cells were derived from progeny of transgenic mice expressing SV40 large T-antigen under control of the rat insulin II 5'-flanking region or rat preproglucagon 5'-flanking region, respectively (Powers et al, 1990) and were originally provided by Douglas Hanahan (Department of Biochemistry and Biophysics, University of California, San Francisco, Calif.). βTC3 were grown in RPMI 1640 11 mM glucose, supplemented with 10% heat inactivated fetal bovine serum, 2 mM L-glutamine, and 100 IU/ml streptomycin/penicillin, as previously described (Galbiati et al, 2002). Experiments were performed between the 27 and 33 passage of cell culture.

αTC1 were cultured in DMEM 25 mM glucose supplemented with 10% heat inactivated fetal bovine serum, 2 mM glutamine, and 100 IU/ml streptomycin/penicillin, as previously described (Galbiati et al, 2002). Experiments were performed between the 33 and 43 passage of cell culture. Cells were cultured under standard humidified conditions of 5% $CO_2$ at 37° C.

Cos cells, were cultured in DMEM supplemented with 10% fetal bovine serum, 2 mM glutamine, and 100 IU/ml streptomycin/penicillin. All media were supplied by SigmaAldrich.

Human Islets Isolation and Culture

Human pancreatic islets were isolated from the pancreases of cadaveric multiorgan donors by using the procedure already described by Ricordi (Ricordi, et al, 1988). The islets used in this study were isolated from eight different organs. After the isolation, the islets were purified from the contaminant exocrine tissue by centrifugation on Ficoll gradients, obtaining a final purity that ranged from 60% to 80%, as assayed by dithizone staining (Ricordi et al, 1988). Islets were then cultured in RPMI 1640 tissue culture medium. After a 48-h stabilization culture, old medium was replaced with fresh medium and islets were cultured until used for insulin secretory studies, RNA extraction and uptake experiments. For apoptosis assay, fresh medium containing glutamate (0.5 or 5 mM) or DHK (0.05 or 0.1 mM) was replaced and islets were cultured for additional five days.

[$^3$H]D-aspartic Acid Uptake 150.000 cells/well were plated in a 24-wells plate, and grown until confluence. After two washes in sodium-free solution (150 mM ChCl, 2 mM KCl, 1 mM $CaCl_2$, 1 mM $MgCl_2$, 10 mM Hepes pH 7.5), cells were incubated for 10 minutes in 200 μl of $Na^+$-dependent (150 mM NaCl 2 mM KCl, 1 mM $CaCl_2$, 1 mM $MgCl_2$, 10 mM Hepes pH 7.5) or $Na^+$-independent (sodium-free solution) uptake solution containing 5 μCi/ml of [$^3$H]D-Aspartic acid (specific activity 37 Ci/mmol; Amersham Biosciences). The amino acid uptake was stopped by washing the cells twice in ice-cold sodium-free solution. Cells were dissolved in 150 μl of SDS 1% for liquid scintillation counting. For transport inhibition, DHK was added to the uptake solution at the indicated concentrations.

Diagnostic Functional Assay for the Determination of Anti-GLT1 Antibodies in the Serum of DMT1 Patients βTC3 cells were plated in a 96-wells plate, and grown for two days. After one wash in RPMI medium, cells were incubated with 20% human serum samples in sodium solution (150 mM NaCl 2 mM KCl, 1 mM $CaCl_2$, 1 mM $MgCl_2$, 10 mM Hepes pH 7.5) or normal medium for 3 hours at 37° C. Then cells were washed twice with Na-free uptake solution (150 mM ChCl, 2 mM KCl, 1 mM $CaCl_2$, 1 mM $MgCl_2$, 10 mM Hepes pH 7.5), and incubated in 50 μl of $Na^+$-dependent (150 mM NaCl 2 mM KCl, 1 mM $CaCl_2$, 1 mM $MgCl_2$, 10 mM Hepes pH 7.5) uptake solution containing 5 μCi/ml of [$^3$H]D-Aspartic acid (specific activity 37 Ci/mmol; Amersham Biosciences). The amino acid uptake was stopped by washing the cells twice in ice-cold sodium-free solution. Cells were dissolved in 50 μl of SDS 1% for liquid scintillation counting. The controls are uptake experiments performed in the absence of serum pre-incubation. The non-GLT1-mediated glutamate/aspartate uptake is calculated performing uptake experiments in the presence of 0.3 mM DHK. 12 serum samples from control subjects and 23 from DMT1 patients were analysed.

RNA Isolation and RT-PCR Analysis

βTC3 and αTC1 cells were plated onto 6 cm Petri dishes and grown until confluence. 3 ml of RNAFast were added to culture dishes and the total RNA was extracted with RNA fast isolation system following manufacturer's protocol (Molecular Systems-San Diego, Calif.). After RNA precipitation, pellet was resuspended in 15 µl of UltraPure™ DNase/RNase-Free Distilled Water (Gibco, Invitrogen) to obtain adequate concentration for subsequent reactions.

Total RNA quality was controlled by electrophoresis and its concentration was measured by means of spectrophotometric absorbance. A similar protocol was used to extract total RNA from 1500 isolated human islets of.

To remove any DNA contamination from RNA extract, 2 mg of total RNA were digested with DNAse (Promega) in the presence of RNAse OUT (Invitrogen) for 30 minutes at 37° C. The reaction was stopped by 10 minutes incubation with Stop Solution (Promega) at 65° C. For cDNA synthesis, 2 µg of digested RNA was reverse-transcribed using random oligonucleotides (final concentration 12.5 ng/µl; Promega) as a primers, and 200 U of M-MLU reverse transcriptase (Invitrogen) in the presence of RNAse OUT, DTT 0.1 M (Invitrogen) and dNTPs (Promega). In the first step, RNA, oligonucleotides and UltraPure™ DNase/RNase-Free Distilled Water were incubated at 65° C. for 5 minutes; then the other reagents were added and the reaction was incubated for 50 minutes at 37° C. PCR amplification of the reverse-transcribed RNA was carried out using specific primers, designed with the help of the software Primer Input 4.0 (available on line) in the 3' end of each cDNAs in order to give a product of 200 bp.

The following primers were used

| Mouse cell lines | | | Sequence | PCR product |
|---|---|---|---|---|
| Mouse GLT1a | Forw Rev | 1563 1736 | gaccaagacgcagtccattt ggctgagaatcgggtcatta | 193 |
| Mouse GLT1b | Forw Rev | 1573 1743 | gaccaagacgcagtccattt gatgcaagggttgtgattt | 190 |
| Mouse GLAST | Forw Rev | 2005 2780 | atgttgaaatggggaactcg gccgttttccaatcctatca | 300 |
| Mouse EAAC1 | Forw Rev | 1483 1773 | ggagcagatggatgtttcgt gctaggagatggctcctgtg | 310 |

| Human Islet of | | | Sequence | PCR product |
|---|---|---|---|---|
| Human GLT1a/EAAT2 | Forw Rev | 1743 1953 | cttttggggctgggatagtc ttggctgccagagttacctt | 211 |

For tubulin amplification see Federici et al, 2001. Reaction was performed with PCR Master Mix (Promega) in 25 µl volume.

Cycling conditions were 2 minutes at 95° C.; 30 seconds at 95° C., 30 seconds at 60° C., 1 minute at 72° C., for 40 cycles; and a final elongation at 72° C. for 10 minutes. Amplified DNA fragments were analyzed by electrophoresis in a 1.5% agarose gel and compared to 250 bp ladder (Invitrogen). To confirm absence of genomic contamination in the RNA samples, reverse transcriptase-negative controls were introduced in each experiment (in the RT-PCR, the M-MLU reverse transcriptase was omitted).

MouseGLT1 and ratEAAC1 Cloning

The full-length coding sequences of rat EAAC1 (147-1845 bp, GenBank™ accession number U39555) and mouse GLT1 (31-1754 bp, GenBank™ accession number AB007811) were cloned from rat kidney or mouse brain cRNA by RT-PCR reaction. First-strand cDNA was synthesized using Moloney murine leukemia virus reverse transcriptase and specific primers localized in the 3' untranslated region of rat EAAC1 and mouse GLT1. Amplification of full length transporters was obtained by PCR reactions using specific oligonucleotides primers designed with the assistance of the Primer3 software (http://primer3.sourceforge.net/; Rozen and Skaletsky 2000) in the 5' and 3' untranslated regions of ratEAAC1 and mouseGLT1. To facilitate the directional cloning of the fragment in plasmid vectors, a second PCR was carried out using primers carrying a BamHI enzyme restriction sites (mouse GLT1). PCR products were cloned into pCDNA vector, and sequence verified.

Cell Lysis and Western Blotting Analysis $\beta TC_3$ or $\alpha TC_1$ cells were seeded onto 6-cm tissue culture plates and allowed to attach and grow until confluence. Cells or 1500 isolated human islets were harvested and lysed in 100 µl lysis buffer (150 mM NaCl, 30 mM Tris-HCl, 1 mM $MgCl_2$, 1% Triton X-100, 1 mM phenylmethylsulfonylfluoride, and 1 µg/ml aprotinin and leupeptin). After 1 h at 4 C, lysates were centrifuged at 13,000 rpm for 10 min, and 50 µg of total extracted proteins were analyzed on 9% SDS-PAGE and transferred onto nitrocellulose (Shleicher and Shull, Dassel, Germany). The blots were probed with rabbit anti-EAAC1 (Alpha Diagnostic) and anti-GLT1 (1 µg/ml; kindly provided by dr. Grazia Pietrini, Perego et al., 2000 or Alpha Diagnostic) antibodies as a primary reagent followed by anti-rabbit or anti-human (80 ng/ml; Amersham, GE Healthcare) HRP-conjugated IgG, and visualised by ECL (Perkin-Elmer Life Science, Boston, Mass.). The signal intensities were densitometrically quantified using Scion Image software.

P2 Extract:

Total homogenates of rat brain tissues were prepared in a medium containing 0.32 M Sucrose, 10 Mm Tris-HCl pH 7.5, 5 mM EDTA, 5 mM EGTA and a mixture of protease inhibitors. After homogenization and centrifugation, the two supernatants were mixed and ultracentrifugated at 37000 g for 40 minutes at 4° C. The deriving pellet was resuspended in 10 volumes of RIPA buffer (150 mM NaCl, 50 mM TrisHCl pH 7.5, 1 mM EDTA, 1% NP-40, 0.5% deoxycholate, 0.05% SDS and a mixture of protease inhibitors) followed by 45 minutes incubation at 4° C. under constant agitation. Lysate was clarified by 10 minutes centrifugation at 13000 rpm, separated by SDS-PAGE and transferred to nitrocellulose.

Immunoprecipitation 50-100 mg of rat-P2 brain proteins or $\beta TC_3$ lysates-proteins were 0/N incubated at 4° C. with 4 µl of the anti-GLT1 antibody (Perego et al, 2000), 4 µl of preimmune rabbit serum or 15 µl of human serum samples. Then, 40 µl of 50% protein A sepharose (Immunopure Immobilized Protein A, Pierce) were added to each sample, incubated for two hours at 4° C. and the beads were recovered by centrifugation. Beads were then washed several times with the lysis buffer. After a final washing in 50 mM TrisHCl, pH 8, proteins bound to the beads were solubilised with LB and separated by SDS-PAGE.

Cell Transfection $3 \times 10^5$ COS or $\beta TC_3$ cells/cm² were seeded onto tissue culture dishes and, 24 hours after plating, they were transfected with rat EAAC1, mouse GLT1 or shRNA (Origene) by means of lipofection (Lipofectamine™ 2000 reagent, Invitrogen). 48 hours after transfection, cells were processed for immunofluorescence.

Immunofluorescence

Cell Cultures.

βTC3 and COS cells were plated onto sterile glass coverslips. 48 hours after COS transient transfection and after βTC3 growth until 70% of confluence, COS and βTC3 cells were fixed in ice-cold methanol for 10 minutes and permeabilised with 0.5% Triton X-100 in PBS. Immunostaining with the primary antibodies in GDB solution (75 mM NaCl, 5 mM PO$_4$ buffered saline pH 7.4, 0.25% Triton X-100, 0.1% gelatine) was followed by incubation with the appropriate secondary antibodies (FITC-conjugated anti-rabbit, Rhodamine-conjugated anti-mouse or FITC-conjugated anti-human IgG, from Jackson Immunoresearch (West Grove, Pa.). The following primary antibodies were used: rabbit anti-GLT1 (Perego et al., 2000) and anti-EAAC1 antibodies (Alpha Diagnostic), control and T1D sera (for serum samples characterization see Table A).

Paraffin Embedded Sections.

Normal human pancreas were fixed in buffered formalin (formaldehyde 4% w/v and acetate buffer 0.05 mol/L) for 24 hours and then routinely processed and paraffin embedded. 5 μm thick sections were mounted on poly-L-lysine coated slides, deparaffinized and hydrated through graded alcohol to water. After heat antigen retrieval, performed using microwave oven in 10 mM Citrate Buffer pH 6, sections were permeabilized using TBS-Triton 0.2%. Primary antibodies incubation was performed over night at 4° C. in the following solution: 0.2% Triton X-100, 1% gelatine in TBS pH 7.4. Then sections were washed thoroughly in TBS-Triton 0.2% and incubated with secondary antibodies for 2 hours at room temperature, followed by fluorochrome-conjugated streptavidin incubation for 30 minutes. The followed primary antibodies were used: guinea pig anti-insulin (Roche); mouse anti-glucagone (R&D Systems); mouse anti somatostatin (Biomeda); mouse anti-chromogranin (Biogenex); rabbit anti-GLT1 (Perego et al., 2000). Secondary antibodies (FITC-conjugated anti-mouse IgG and biotin-conjugated anti-rabbit IgG) were from Jackson laboratories.

Immunohystochemistry

ABC immunohystochemistry was performed in formalin fixed human pancreas paraffin embedded sections. To suppress possible endogenous peroxidase activity, pancreas sections were treated with an hydrogen peroxide solution before antigen retrival by microwave heating in citrate buffer. Sections were permeabilized with 0.3% Triton in TBS and incubated in normal anti donkey serum for 40 min at room temperature, to reduce unspecific protein binding, then they were incubated with rabbit anti-GLT1 antibody o/n at 4° C. Unbound antibodies were washed with TBS-Triton 0.3% and the signal was amplified using biotin-conjugated secondary antibodies (anti-rabbit biotin, Jackson) for 2 hours at room temperature, followed by Peroxidase conjugated-streptavidin (Chemicon). The reaction was performed with freshly activated DAB (Diaminobenzidine, Sigma Aldrich). Colour development was stopped by washing the slides thoroughly in tap water. The sections were then counterstained with Mayer's hematoxylin, and dihydratated. Coverslips were mounted with an hydrophobic mounting medium (Dako Corp.).

Cell Viability Assay 3-(4,5-Dimethylthiazol-2-yl)-2,5-diphenyltetrazolium bromide (MTT) assay. βTC$_3$ cells were seeded at a density of $8 \times 10^3$ cells/well onto 96-well culture plates. Cells were allowed to attach and grow for 24 h in standard medium. Then medium was replaced with fresh medium containing glutamate, DHK (Dihydrokainic Acid, Sigma Aldrich), glutamate receptor inhibitors APV and CNQX (Sigma Aldrich) or ceftriaxone (Sigma Aldrich) at the indicated concentrations. After five days incubation, cell viability was assessed using the MTT method, according to the manufacturer's protocols (Sigma Aldrich). Coloured formazan product was determined spectrophotometrically at 540 nm. 20 islets/tube were used to assess viability in human isolated islets. Data are expressed as % Relative Growth Rate (% RGR) versus control samples.

Quantification of Apoptosis in βCells and Isolated Human Islets

Apoptosis of β-TC3 cells was estimated using the terminal deoxynucleotidyltransferase-mediated dUTP-biotin nick end-labelling assay (TUNEL). Briefly, $3 \times 10^5$ βTC3 cells were plated on glass coverslips, and 24 hours after plating, they were incubated with glutamate or DHK at the indicated concentration for five days. Control and treated cells were fixed in 4% paraformaldehyde, permeabilized using 0.5% Triton X-100 for 4 minutes at room temperature and processed according to the manufacturer's instructions. Tunel-positive cells were counted by two independent observers using a 40× objective from at least 40 randomly selected fields per coverslip. Data were plotted as number of death cells/field.

Insulin Secretion

Insulin content and secretion were assessed on 20 islets, using a Micro-particle Enzyme Immunoassay (MEIA insulin, IMX System, Abbott Laboratories, Abbott Park, Ill., USA). Insulin secretion in response to increasing glucose concentrations, glutamate or DHK treatment was assessed by static incubation as previously described (Federici et al, 2000). Briefly, batches of 20 islets were pre-incubated in 1 ml of Krebs-Ringer buffer (KRB) supplemented with 3, 3 or 16.7 mM glucose for 30 min. Then the supernatants were replaced with Kreb's buffer containing 3, 3 or 16.7 mM glucose plus glutamate or the specific GLT1 inhibitor DHK (Sigma, St Louis, Mo., USA), as indicated. After a 30-min incubation at 37° C., the medium was removed and frozen for immunoassays. At the end of incubation, islets were lysed in lyses buffer and the total insulin content determined by immunoassay. Levels of secreted insulin from islets were normalized to total insulin content.

Co-Localization Analysis

Single channel images obtained with the BIORAD confocal microscope (GLT1: channel 1/red; hormones: channel 2/green) were analyzed for pixel intensity with the JImage software. Co-localization between the two channels was calculated with a computer assisted program. The product of the differences from the mean intensity (PDM value) was calculated in each location of the image as indicated:

$$PDM = (\text{red intensity} - \text{mean red intensity}) \times (\text{green intensity} - \text{mean green intensity}).$$

If the intensities in the two channels vary in synchrony (i.e. they are dependent), they will vary around their respective mean image intensities together and the PDM value will be positive. If the pixel intensities vary asynchronously (i.e. the channels are segregated) most of the PDM value will be negative. A PDM positive value is indicative of co-localization, vice versa a negative value indicates segregated staining.

The Intensity Correlation Quotient (ICQ) was calculated on the entire area and was ICQ=(number of positive PDM)/(total number of PDM)−0.5

Random staining: ICQ~0;
Segregated staining: 0>ICQ³−0.5;
Dependent staining: 0<ICQ³+0.5

For chromogranin and insulin, the PDM value was calculated on the entire islet; for glucagon and somatostatin, analysis was performed on the particular showed at higher magnification.

Statistical analysis. Statistical significance of difference between groups was determined by unpaired Student's t-test. Differences were considered significant at $P \leq 0.05$.

Serum Samples:

Serum samples from 14 healthy subjects (negative control) and 21 who have been given a diagnosis of T1D were collected and stored at −20° C. until used. Details are provided in table A.

TABLE A

|  | Normal | Diabetic |
| --- | --- | --- |
| Sex (F/M) | 5/9 | 12/9 |
| Age (years) | 17.5 ± 10.9 | 32.3 ± 5.3 |

Tissue Samples:

Human pancreas from control or T2D patients were obtained from autopsic patients or surgically removed tumors. The samples were immediately fixed in 4% formaldehyde for immunocytochemical analysis. The phenotypic data of the group of patients with type 2 diabetes and Controls, used for immunohystochemical studies in this report, are provided in Table B.

TABLE B

|  | Normal | Diabetic |
| --- | --- | --- |
| Sex (F/M) | 3/3 | 4/3 |
| Age (years) | 64.5 ± 10.9 | 67.6 ± 5.3 |
| Duration of DM (years) | 0 | 10.2 ± 2.8 |

Results

Figure 1B:
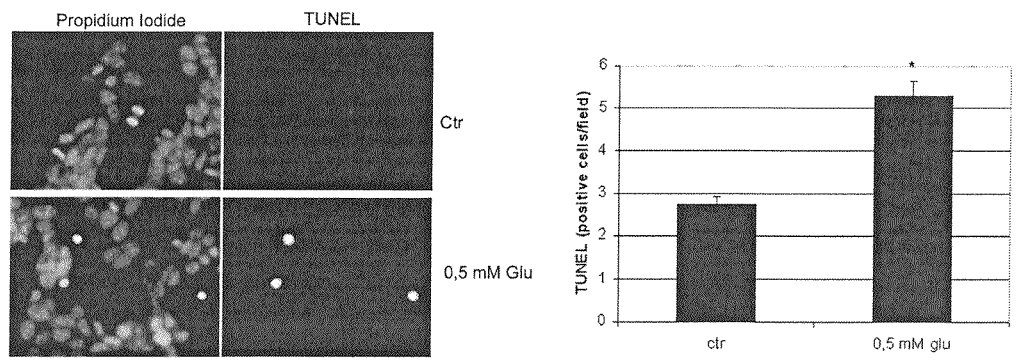

Glutamate is Toxic to Endocrine β-Cells and Glutamate Toxicity May be Prevented by Inhibition of Ionotropic Glutamate Receptors We first determine whether glutamate application may cause endocrine cell death. βTC3 and αTC1 cell lines were cultured for five days in the presence of different glutamate concentrations (from 0.05 to 5 mM), and cell viability was assessed by means of MTT test (FIG. 1A). Prolonged exposure to glutamate resulted in sustained reduction of βcell viability: β-cell toxicity was already detectable at 0.05 mM glutamate (11.53+0.52% reduction in RGR; $p<0.01$) and it was maximal at 5 mM glutamate (51.46+2.61% reduction in RGR; $p<0.01$). In contrast to βTC3, in αTC1 cells glutamate toxicity was detectable only at the highest glutamate concentration (5 mM) but significantly lower than in βTC3 ($p<0.01$) (FIG. 1B).

We did not find any effect on cell survival after acute exposure to glutamate (15 min, 0.5 µM glutamate: a treatment effective on neurons, Perego et al, 2000), or after exposure to glutamate for 2 days, both in αTC1 and in βTC3 cells.

The different viability of βTC3 and αTC1 cells cultured for 5 days in the presence of high glutamate concentrations was not due to differences in medium composition (RPMI for βTC3 and D-MEM for αTC1), since cell death was even more pronounced in D-MEM medium. These data indicate that β-cells, like neurons, are vulnerable to the toxic effects of glutamate even though to a much lesser extent, as expected.

To further investigate the mechanisms by which chronic glutamate exposure may cause β-cell cytotoxicity, we performed a TUNEL assay. As shown in FIG. 1B, culture of βTC3 cells in presence of 0.5 mM glutamate for 5 days resulted in a significant increase in the number of TUNEL positive cells, indicating that glutamate induces β-cell death by apoptosis.

Figure 1C:
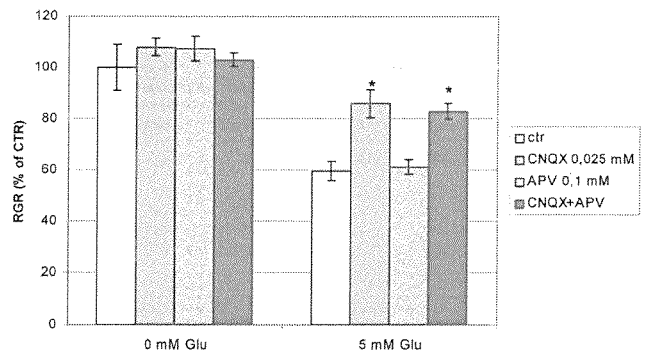

In the CNS, glutamate toxicity is caused by persistent activation of ionotropic receptors which are also expressed by pancreatic islet cells (Choi, 1988; Matute et al, 2007). To determine whether glutamate-induced β-cell death is mediated by the same mechanisms involved in neurotoxicity, ionotropic channels were blocked with their antagonists, in the presence of 5 mM glutamate (FIG. 1C). Vulnerability of β-cells to glutamate was partially prevented by co-administration of glutamate with 6-Cyano-7-nitroquinoxaline-2,3-dione (CNQX), a non-selective AMPA and kainate receptor antagonist (30% increase in RGR relative to 5 mM glutamate; $p<0.05$) but not D-2-Amino-5-phosphonovaleric acid (APV), a selective NMDA receptor antagonist. No significantly differences in β-TC3 viability were detected in the presence of glutamate receptor antagonists, when given alone. These data indicate that glutamate-mediated β-cell cytotoxicity, as in the CNS, is mediated by extracellular glutamate and is triggered by the activation of AMPA and/or kainate ionotropic glutamate receptors.

The Na-Dependent Glutamate Transporter GLT1A is Exclusively Expressed by βTC3 Cells.

In the CNS, the extracellular glutamate concentration is maintained at relatively low levels by high-affinity glutamate transporters and in particular by GLT1. Although a high-affinity glutamate transporter has been cloned from pancreas (Manfras et al, 1994) and D-aspartate accumulation has been demonstrated in pancreatic islets (Weaver et al, 1998), it is not clear the pattern of expression of the different glutamate transporter types in endocrine cells. To this purpose, RT-PCR experiments were carried out using type-specific primers in αTC1 and βTC3 cells. RT-PCR (35 cycles) of total RNA from βTC3 cells resulted in the amplification of the GLT1A type, while all the other types were undetectable even after 40 PCR cycles. None of the canonical high-affinity glutamate transporters were detected in αTC1 cells after 40 cycles.

Figure 2A:
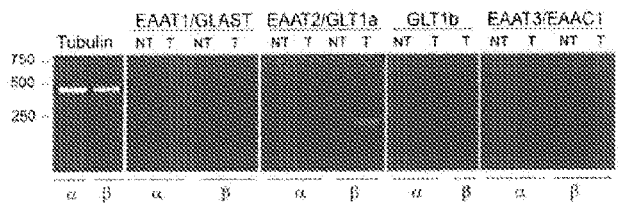
Figure 2B:
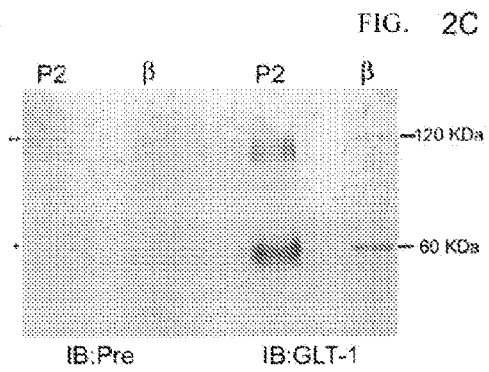

Western blotting experiments confirmed the exclusive expression of GLT1 in the βTC3 cells. As shown in FIG. 2B, a previously characterized anti-GLT1 antibody (Perego et al, 2000) identified two bands, running with an electrophoretic mobility of 60 and 120 KDa, in immunoblots of βTC. The molecular weight of these bands correspond with the molecular weight of GLT1 proteins identified in brain samples, thus confirming the expression of GLT1 in β-cells. No bands were detected using a pre-immune serum or anti-GLAST and anti-EAAC1 antibodies.

Figure 2C:
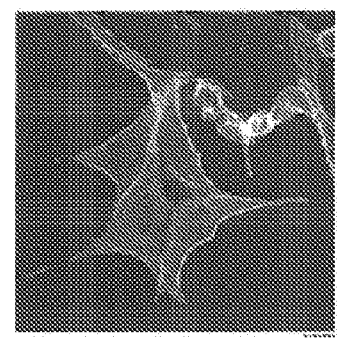

Immunofluorescence studies performed with the anti-GLT1 antibody revealed that the transporter was expressed in the vast majority of βTC3 cells and that it was prevalently located at the cell membrane where it could fulfil its function (FIG. 2C). No staining was detected in αTC1 cells or when the primary antibody was omitted.

Figure 2D:
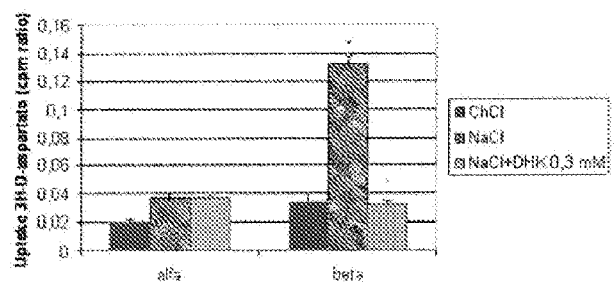

To characterize the presence of functional transporters, experiments of 3H-D-aspartate (a non-metabolized GLT1 substrate Danbolt, 2001) uptake were performed in αTC1 and βTC3 cells. As shown in FIG. 2D, αTC1 and βTC3 cells showed a similar Na-independent (ChCl) 3H-D-aspartate uptake. Conversely, Na-dependent D-aspartate uptake was significantly higher in βTC3 than in αTC1 cells.

Subtype specific expression of glutamate transporters was analyzed pharmacologically using dihydrokainate (DHK) a selective GLT1 inhibitor (Arriza et al., 1994). Na-dependent aspartate uptake in βTC3 was completely inhibited in the presence of 1 mM DHK, indicating that glutamate uptake in these cells is exclusively driven by GLT1. On the contrary, in αTC1 cells Na-dependent D-aspartate uptake was not inhibited by DHK, confirming that these cells express very low level of the GLT1 transporter, alternatively, they may express an unidentified glutamate type/s.

Figure 3A:
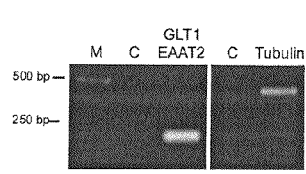

To determine whether the β-cell-exclusive expression of GLT1 observed in cell lines occurs also in vivo, the expression and the localization of the transporter was analyzed in human isolated islets and human pancreas sections (Varese and HSR). Human islets were isolated as described by Ricordi (Ricordi et al, 1988) and the expression of the glutamate transporter GLT1a was assessed by RT-PCR (FIG. 3A), immunoprecipitation (FIG. 3B) and uptake experiments (FIG. 3C). RT-PCR of total RNA with human type-specific primers resulted in amplification of the GLT1a type of glutamate transporter (35 cycles) (FIG. 3A).

Figure 3B:
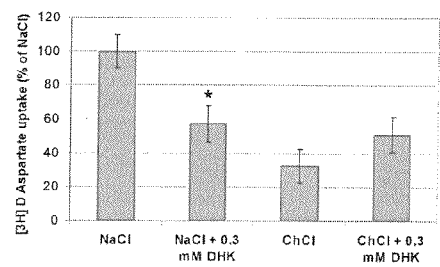
Figure 3C:
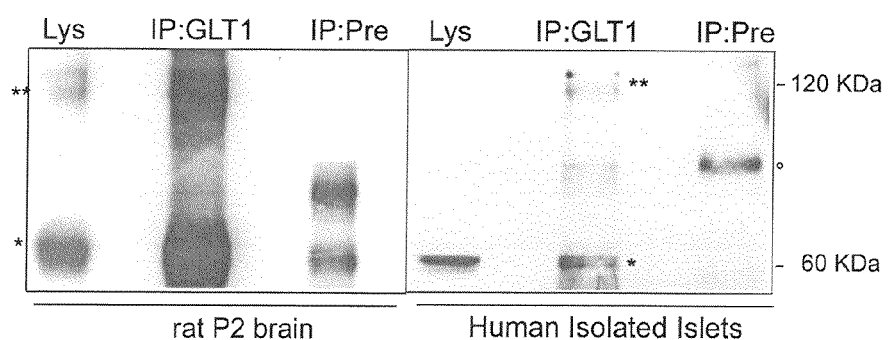

Immunoprecipitation and western blotting experiments confirmed the expression of GLT1 in islet of human pancreas (FIG. 3B). In SDS-PAGE, the anti-GLT1 antibody revealed the presence of bands running with an apparent electrophoretical mobility of 60 and 120 KDa and corresponding to the monomeric and oligomeric form of GLT1, respectively, in both islets and brain immunoprecipitates.

The function of GLT1 was assessed by measuring D-aspartate uptake (FIG. 3C). A clear Na-dependent transport of aspartate was present in isolated human islets and was completely inhibited by 0.1 mM DHK. Taken together, these data show that pancreatic islets express a functional glutamate transporter and that GLT1 is the main regulator of glutamate clearance in human islets.

Figure 4A:
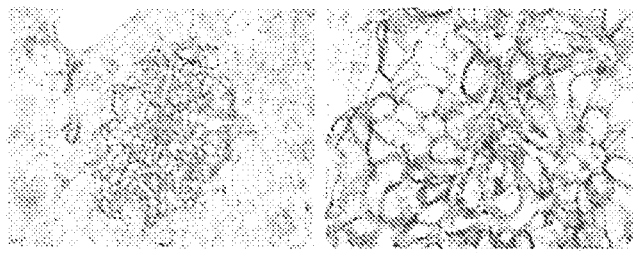

In order to confirm the β-cell specific expression of GLT1 in vivo, immunocytochemical and experiments were carried out in human pancreas sections. As shown in FIG. 4A, anti-GLT1 reactivity was restricted to a group of clustered cells, most likely correspondent to an islet. Noteworthy, few cells in the islet's core were completely devoid of GLT1 signal, thereby suggesting a cell-specific expression. At higher magnification, GLT1 staining was confined to the cell membrane, a localization consistent with the physiologic role of this transporter.

No staining for EAAC1/EAAT3 or GLAST1/EAAT2 was detected in the endocrine pancreas.

Figure 4B:
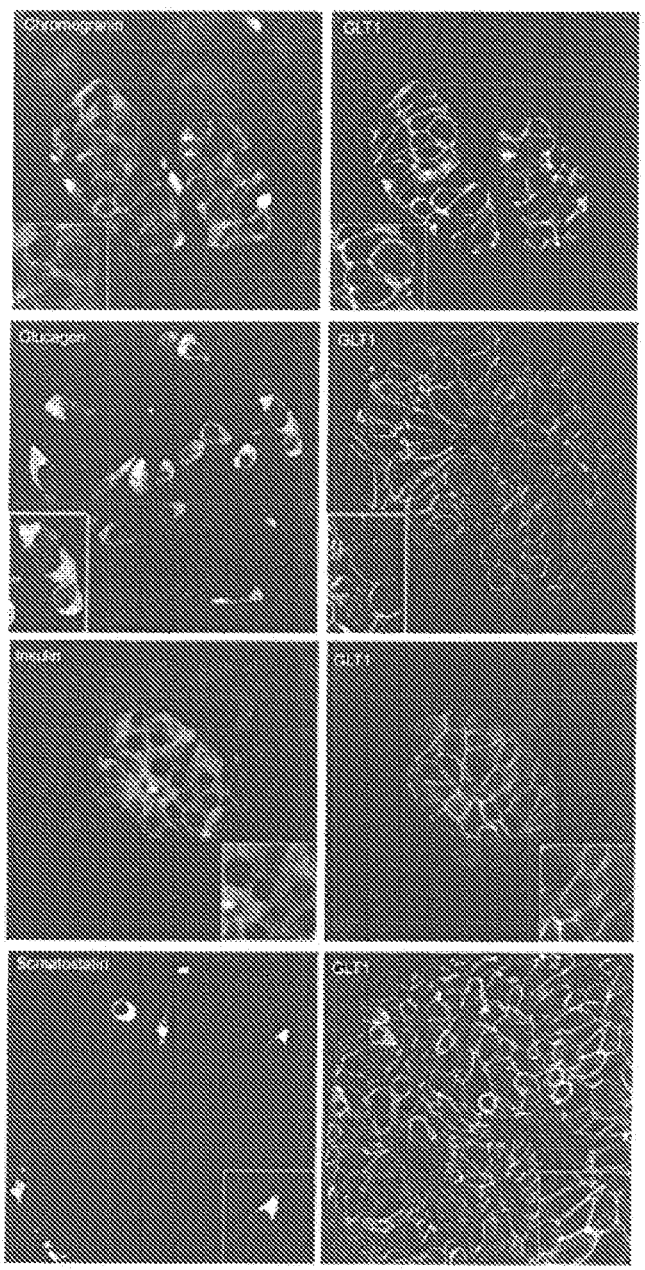

To identify which of the islet endocrine cell types expresses GLT1a, double immunofluorescence experiments were carried out using the anti-GLT1 antibody and hormones as markers of the different cell types (FIG. 4B). Immunostaining with chromogranin, a marker of endocrine cells, confirmed the expression of GLT1 only in the islets. GLT1 signal was concentrated at, or immediately below, the plasma membrane where it co-localized with chromogranin granules fused to the cell membrane; no intracellular GLT1 staining was detected. Similar staining at the cell-cell boundary was detected in the majority of insulin-positive cells in the islet core, indicative of GLT1 expression in β-cells. On the contrary, GLT1 was not observed at the plasma membrane of glucagon-positive cells. These data suggest that GLT1 is not expressed in the plasma membrane of α and δ-cells, or if expressed, is under the level of detection. These conclusions were supported by a computer-assisted image analyses system (Table I). To mathematically evaluate co-localization between GLT1 (channel1) and hormones (channel2), the PDM value (product of the differences of pixel intensity from the mean intensity of each channel) was calculated. As shown in Table I, the intensity correlation quotient (ICQ=(number of positive PDM)/(total number of PDM)–0.5), calculated on the entire area, was positive for the insulin/GLT and chromogranin/GLT double immunostainings, thus indicating that there was co-localization. On the contrary, the negative ICQ value calculated for the glucagon/GLT1 and somatostatin/GLT1 double immunostaining, was indicative of segregated stainings. Taken together these data demonstrate that GLT1 is mainly expressed in β-cells.

Table I. Co-Localization Analysis

Co-localization between GLT1 and hormoneS was calculated with a computer assisted program. Single channel confocal images were analyzed for pixel intensity with the JImage software. To mathematically evaluate co-localization between GLT1 (channel 1, red) and hormones (channel 2, green), the product of the differences of pixel intensity from the mean intensity of each channel (PDM value) for the entire area was calculated.

Rr: Pearson' Coefficient for the entire area analyzed

ICQ: Intensity Correlation Quotient=(number of positive PDM)/(total number of PDM)–0.5

Random staining: ICQ~0;

Segregated staining: $-0.5 < ICQ^3 < 0$

Dependent staining: $0 < ICQ^3 < +0.5$ z-score: expresses the divergence of the experimental result from the most probable result as a number of standard deviations. The larger the value of z, the less probable the experimental result is due to chance.

p test: probability confidence, level set at 0.05

Ch1 P: determines if channel 1 is a subset of channel 2

Ch2 P: determines if channel 2 is a subset of channel 1

When the PDM value was calculated on the entire area, negative z score and low p values are due to areas showing exclusive hormone stainings.

PDM values calculated at each location support statistically significant co-localization between GLT1 and insulin or chromogranin at the plasma membrane.

|  | Rr | ICQ | Z score | P (sign test) | Dependent staining |
|---|---|---|---|---|---|
| Chromogranin | 0.567 | 0.514 | −12.563 | >0.050000 | + |
| Insulin | 0.483 | 0.29 | −30.999 | >0.050000 | + |
| Glucagon | 0.099 | −0.307 | −59.524 | >0.050000 | — |
| Somatostatin | −0.265 | −0.367 | −93.294 | >0.050000 | — |

|  | colocal:Ch1 | Ch1 Z score | Ch1 P (sign test) | colocal:Ch2 | Ch2 Z score | Ch2 P (sign test) |
|---|---|---|---|---|---|---|
| Chromogranin | 0.563 | 23.712 | <0.000005 | 0.74 | 79.179 | <0.000005 |
| Insulin | 0.587 | 24.243 | <0.000005 | 0.572 | 20.388 | <0.000005 |

-continued

|  | colocal:Ch1 | Ch1 Z score | Ch1 P (sign test) | colocal:Ch2 | Ch2 Z score | Ch2 P (sign test) |
|---|---|---|---|---|---|---|
| Glucagon | 0.187 | −53.04 | >0.050000 | 0.616 | 10.795 | <0.000000 |
| Somatostatin | 0.203 | −61.14 | >0.050000 | 0.278 | −39.01 | >0.050000 |

Having established the exclusive β-cell expression of GLT1, both in cell lines and in human islet of Langherans, we investigated the role of GLT1 in the islet physiology.

Several independent lines of evidence indicate that glutamate controls secretion of both glucagon and insulin in pancreatic islets, via activation of ionotropic glutamate receptors (Hoy et al, 1995; Inagaki et al, 1995; Muroyama et al, 2004; Bertrand et al, 1993). Therefore, GLT1 controlling the extracellular concentration of glutamate, may affect hormone secretion. FIG. 5 showed the results from a representative experiment where human isolated islets were exposed to 3.3 or 16.7 mM glucose in the absence and the presence of either L-glutamate (0.5 mM), DHK (0.3 mM) or both L-glutamate and DHK, and insulin secretion measured. Insulin secretion was increased in the presence of both glutamate and DHK at 16.7 mM glucose (87±38% increase over the level induced by 16.7 mM glucose control). No effect were detected in the presence of DHK or glutamate alone at 16.7 mM glucose or in any of the conditions tested at 3.3 mM glucose. These data are consistent with a key role of GLT1 in glutamate clearance in the islet, and indicate that this system contributes to the glutamatergic signalling pathway that modulates hormone secretion in the islet.

Figure 6A:
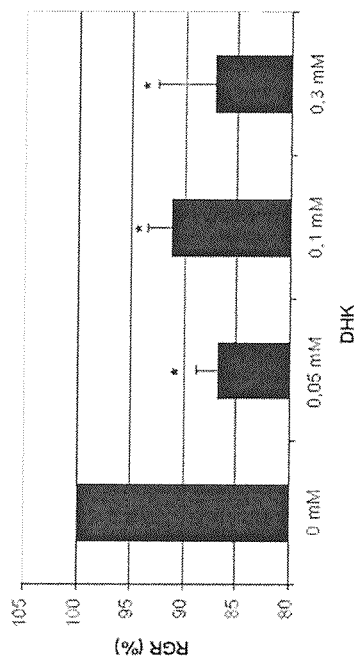
Figure 6B:
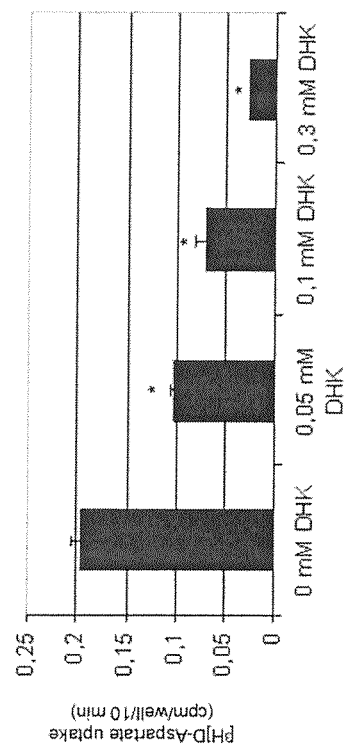
Figure 6C:
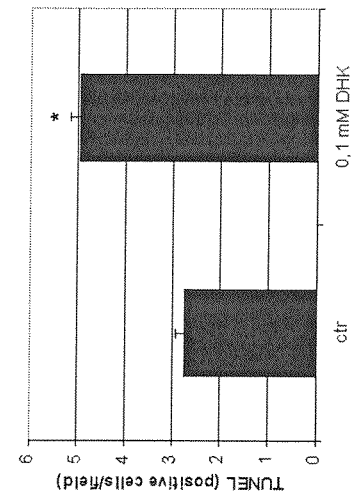
Figure 6C:
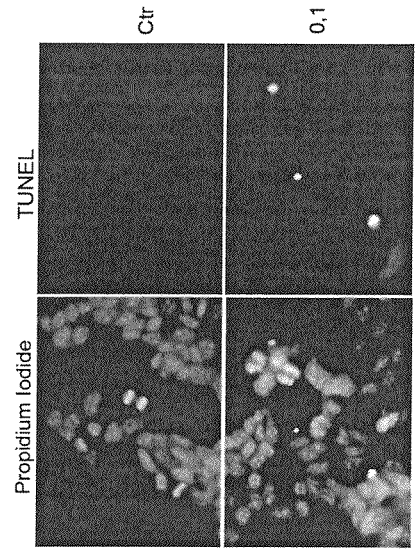

In the CNS GLT1 has been clearly shown to protect neurons from excitotoxicity. Given the vulnerability of βcells to glutamate, we investigate whether inhibition of GLT1 may affect cell survival (FIG. 6). Exposure to DHK induced a dose-dependent inhibition of Na-dependent D-aspartate uptake in βTC3 with IC50=0.05 mM DHK (FIG. 6A). Five days incubation in the presence of the blocker caused a reduction in βTC3 viability that was already maximal at 0.05 mM DHK (6.17% decrease in RGR; p<0.01) (FIG. 6B). Cytotoxicity was due to apoptosis as revealed by a TUNEL assay performed after incubation of βTC3 cells with 0.1 mM DHK for five days (FIG. 6C) (p<0.01).

Figure 6D:
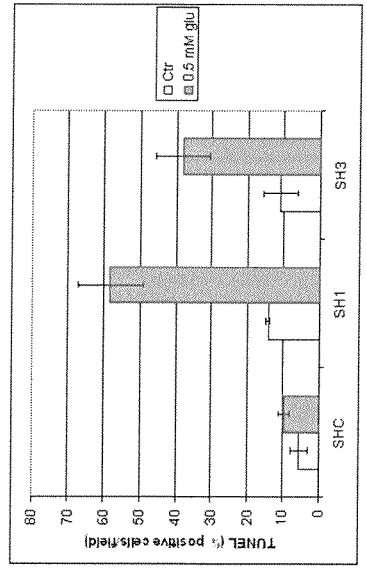
Figure 6D:
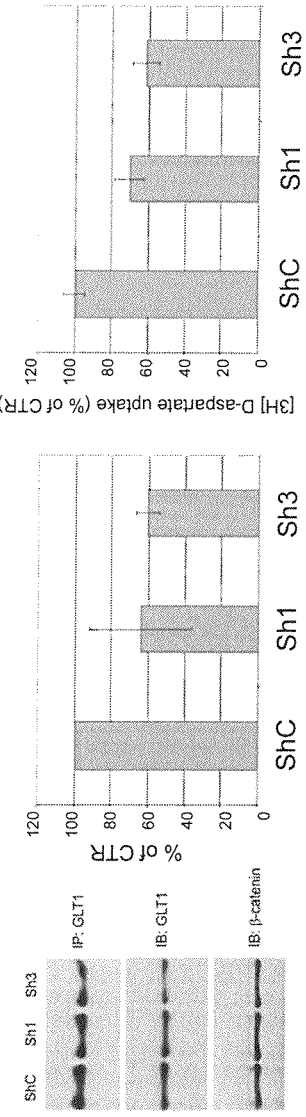
Figure 6D:
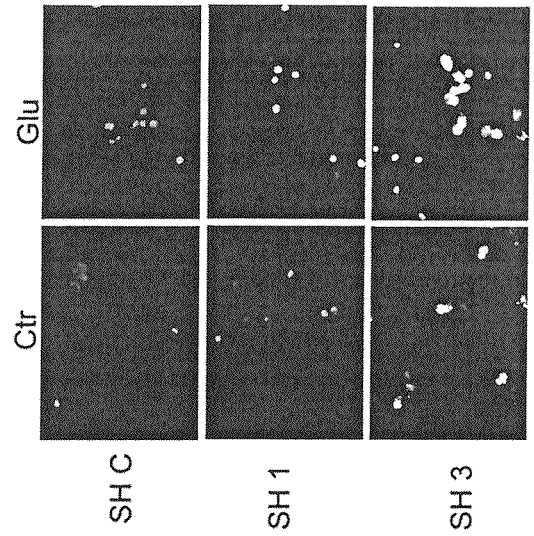

Similar results were obtained after molecular GLT1a knocking down by shRNA. Two different shRNAs (SH1 and SH3) were effective in reducing the GLT1 total expression, as measured by western blotting and uptake experiments (FIGS. 6Da and 6Db). A 30% down regulation in GLT1 surface activity was sufficient to significantly increase cell apoptosis after 24 hour incubation in the presence of 0.5 mM glutamate, as determined by TUNEL assay (p<0.05) (FIG. 6Dc). More interestingly, the SH3 shRNA construct caused increased cell apoptosis also in normal growing medium.

These data, taken together, are consistent with a key role of GLT1 in glutamate clearance and in protecting β-cells from excitotoxicity. Moreover, they indicate that impairment of the GLT1 surface activity is sufficient, by itself, to induce β-cell death at glutamate concentrations proximal to physiological ranges.

Figure 7A:
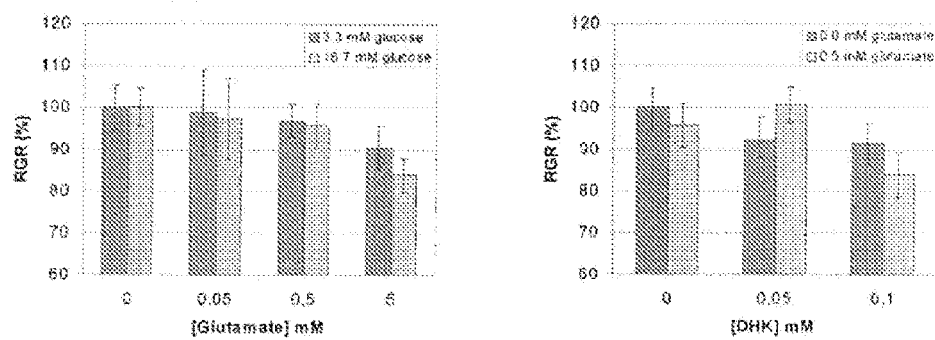
Figure 7B:
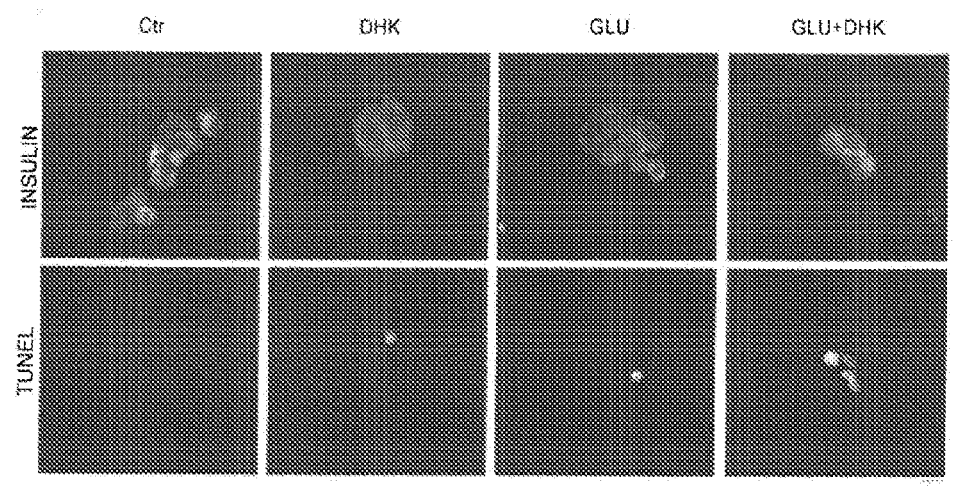

We next tested the vulnerability of human islets to glutamate toxicity. Glutamate incubation for three days caused a dose-dependent decrease in cell viability that reached the statistical significance at the highest glutamate concentration (18% RGR decrease at 5 mM glutamate, p<0.01) in high glucose (16.7 mM glucose), only (FIG. 7A). Interestingly, inhibition of GLT1 with 0.1 mM DHK reduced to 0.5 mM the cytotoxic glutamate concentration (FIG. 7B). Cell death was due to apoptosis (FIG. 7C) and was restricted to β-cells as demonstrated by the TUNEL assay performed on dispersed isolated islets.

Figure 8A:
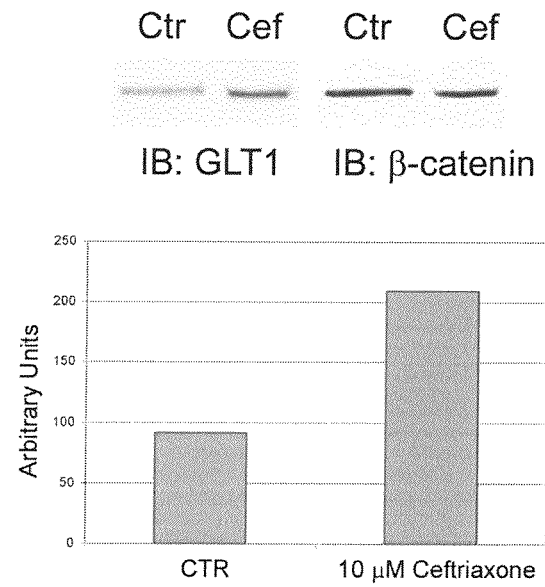
Figure 8B:
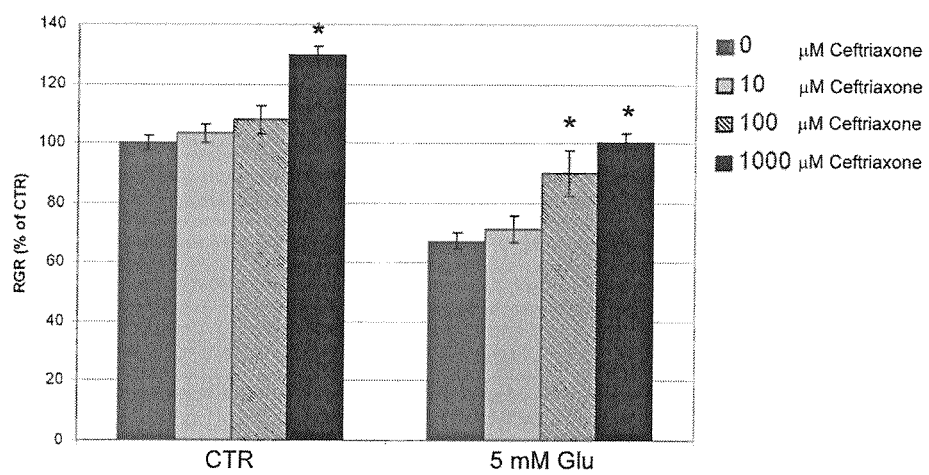

Our data suggest a key role of GLT1 in protecting β-cells from apoptosis, therefore up-regulation of its activity or expression is expected to be β-cell protective. Recently, β-lactam antibiotics were identified as potent stimulators of GLT-1 expression (Rothstein et al. 2005). In particular, the β-lactam ceftriaxone (CEF) was shown to increase both brain GLT1/EAAT2 expression and functional activity in vivo and to be neuroprotective in vitro in models of ischemic injury and motor neuron degeneration, based in part on protection from glutamate toxicity (Rothstein et al. 2003 and 2005). This action appears to be mediated through increased transcription of the EAAT2 gene (Su et al., 2003, Rothstein et al. 2005). 20). Five days incubations with ceftriaxone caused a dose-dependent protection from glutamate toxicity (FIG. 8B). This effect was, at least in part, mediated through GLT1/EAAT2 because increased transporter's expression was measured in the presence of 10 μM ceftriaxone (FIG. 8A).

Our data, taken together, identify glutamate and "excitotoxicity" as new possible pathogenetic factors and demonstrate that the glutamate transporter GLT1 is a key regulator of islet's glutamate clearance and β-cell survival.

Given the selective expression of GLT1 in β-cells, and its direct involvement in cell survival, we hypothesized that GLT1 could have been an important target molecule in diabetes pathogenesis. We therefore examined this possibility in both type 1 and type 2 diabetes, which are both characterized by increased β-cell death and reduced β-cell mass.

Type 1 diabetes (T1D) is a T cell-dependent autoimmune disease, characterized by the selective destruction of islets' β-cells (Anderson and Bluestone, 2005). Autoantibodies against insulin and other antigens expressed by either β-cell and neurons are commonly found in the serum of T1D patients, years before the clinical manifestation of the disease (Bingley et al, 1994; Pihoker et al, 2005; Achenbach et al, 2006). The same autoantibodies are found in some T1D relatives, and their number and titre can predict the progression form prediabetes to diabetes (Tan, 1991). Among them are autoantibodies against insulin (Palmer, et al. 1983), glutamic acid decarboxylase (GAD) (Solimena et al., 1988 and 1990; Baekkeskov, et al. 1990), IA2 (Bonifacio et al, 1995) and the cationic efflux transporter ZnT8 (Wenzlau et al, 2007).

Due to its membrane localization, exclusive for the β-cell, we reasoned that GLT1 could be an ideal T1D autoantigen. In addition to that, given the direct involvement of GLT1 in β-cell survival, autoantibodies against GLT1 may be pathogenetic in sharp contrast with all the autoantigens described to date. At this regard, cytotoxic islet cell surface autoantigens (ICSA) have been described many years ago (Van der Winkle et al, 1982) although their precise identification is still missing.

Therefore, we searched anti-GLT1 antibodies in sera of T1D patients.

Figure 9A:
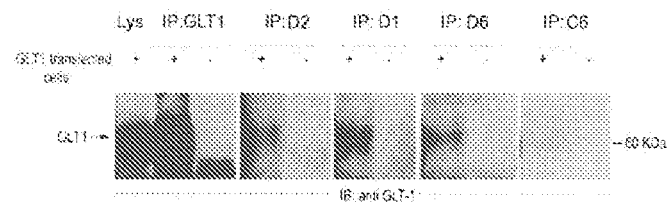
Figure 9B:
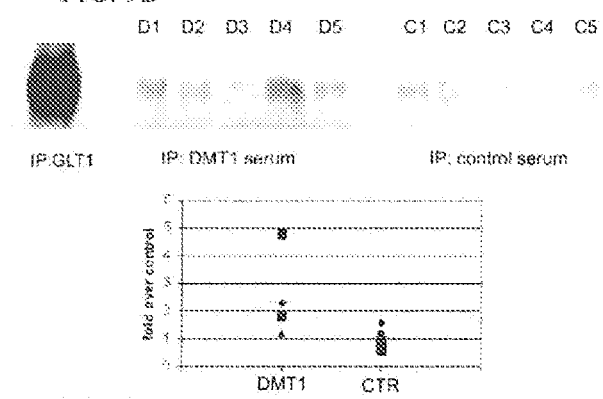

Three T1D sera and 1 control samples were used to immunoprecipitate the corresponding antigen from lysates of GLT1A-transfected COS cells or mock COS cells (FIG. 9A). As a positive control, lysates were immunoprecipitated with the specific anti-GLT1 antibody. As shown in FIG. 9A, the anti-GLT1 antibody immunoprecipitated a protein of 60 KDa from lysates of GLT1-transfected COS cells. The same specific 60 KDa reactivity was detected in immunoprecipitates obtained with sera of T1D patients but not with the control serum, indicative of the presence of anti-GLT1 antibodies in T1D patients.

To further confirm this result, serum from 5 healthy controls (C1-C5) and 5 GAD- and ICA-positive T1D patients (D1-D5), were used to immunoprecipitate the GLT1 protein from the brain P2 fraction (previously shown to contain high amount of native GLT1 protein, FIG. 2). The rabbit-GLT1 immune serum and human sera specifically reacted with a 60 KDa band which correspond to the SDS-PAGE migration of the whole GLT1 protein. Quantification of sera reactivity to the 60 KDa band by densitometry revealed that the mean intensity of immunoprecipitates obtained with sera from T1D patients was 2 fold higher than control sera.

Figure 9C:
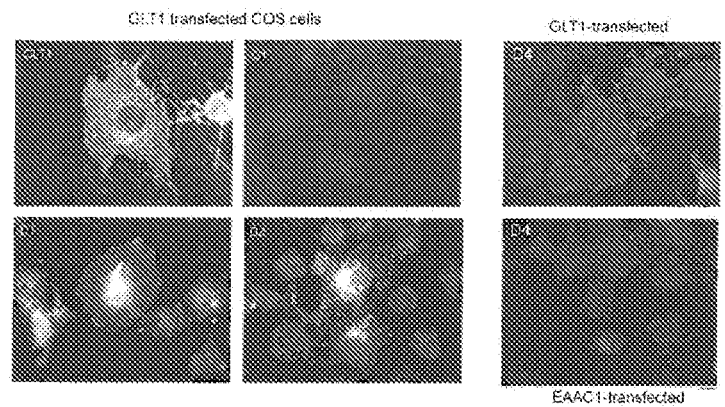
Figure 9D:
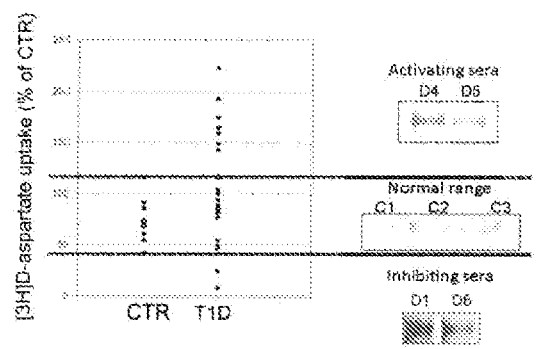

Immunoprecipitation results were confirmed by immunofluorescences studies (FIG. 9C). GLT1 positive sera stained the membrane of COS cells transfected with GLT1A, while no staining was detected with control sera. The detected reactivity was specific for GLT1, since no signal was observed in COS cells transfected with the EAAC1 glutamate transporter.

Finally, we tested the ability of circulating anti-GLT1 autoantibodies to modulate the transporter's activity. β-TC3 cells were incubated with serum samples for three hours at 37° C. and the GLT1 activity measured by uptake experiments. While the control samples showed similar uptake values (100±8.3%), incubation with T1D serum samples caused activity changes ranging from 11.94% to 364.31% relative to control subjects. Considering positive a sample if its uptake value was more then 2SD above or below the mean of controls subjects, we observed that 12 out of 23 T1D (52%) and one out of 12 putative control subjects (8%) were positive. Interestingly, sera found positive with the functional assay, present autoantibodies against GLT1.

Figure 10:
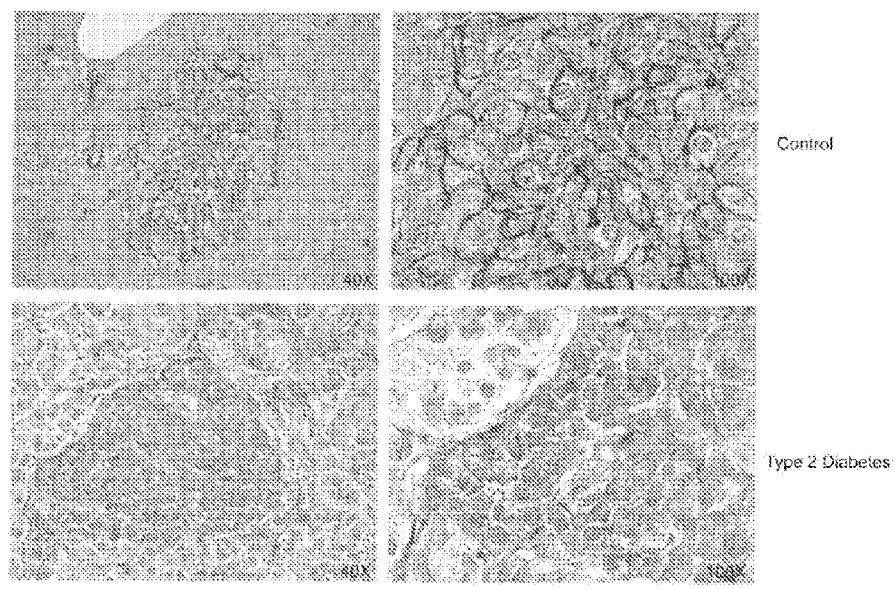

Taken together, these data suggest that GLT1 may represent a novel T1D autoantigen and that anti-GLT1 antibodies may directly modulate the transporter's activity. Therefore, detection of anti-GLT1 antibodies by immunological or functional assays represent new and complementary methods for the diagnosis of T1D. Note that functional assay is rapid, easy to Type 2 diabetes (T2D) is a multifactorial disease characterized by inadequate insulin secretion by pancreatic βcells and impaired insulin action at the target tissues. Insulin resistance, chronic inflammation, oxidative stress, β-cell hypersecretion and amyloid deposition, and hyperglycemia (glucotoxicity) are responsible for the progressive decline in β-cell mass. Increased oxidative stress and chronic inflammation have been shown to directly affect GLT1 expression, localization (Vanoni et al, 2006) and activity (Trotti et al, 1998). We therefore examined by immunocytochemistry (FIG. 10), whether GLT1 was differently expressed in islets of T2D patients. In pancreatic sections obtained from T2D subjects, the typical localization of GLT1 in the cell membrane was completely lost, and GLT1 was exclusively detected in the cytoplasm. Intracellular staining was observed in 5 out of 7 pancreases examined and in none of the 5 pancreases obtained by normal (non diabetic) controls.

Overall, these data indicate that GLT1 is selectively expressed in βcells and glutamate transporter inhibition causes β-cell death mediated by high glutamate. Antibodies against GLT1 were found in serum of T1D patients and GLT1 intracellular staining was detected in T2D patients, thus suggesting a direct role of the transporter in diabetes mellitus pathogenesis or progression.

References

Achenbach P, Warncke K, Reiter J, Williams A J, Ziegler A G, Bingley P J, Bonifacio E. Type 1 diabetes risk assessment: improvement by follow-up measurements in young islet autoantibody-positive relatives. Diabetologia. 2006; 49(12): 2969-76.

Anderson M S, Bluestone J A. The NOD mouse: a model of immune dysregulation. Annu Rev Immunol. 2005; 23: 447-85.

Arriza J L, Fairman W A, Wadiche J I, Murdoch G H, Kavanaugh M P, Amara S G. Functional comparisons of three glutamate transporter subtypes cloned from human motor cortex. *J. Neurosci.*, 1994; 14(9): 5559-69.

Bai L, Zhang X, Ghishan F K. Characterization of vesicular glutamate transporter in pancreatic alpha- and beta-cells and its regulation by glucose. *Am J Physiol Gastrointest Liver Physiol.*, 2003; 284(5): G808-14.

Bertrand G, Gross R, Puech R, Loubatieres-Mariani M M, Bockaert J. Glutamate stimulates glucagon secretion via an excitatory amino acid receptor of the AMPA subtype in rat pancreas. Eur J. Pharmacol. 1993; 237(1):45-50.

Bingley P J, Bonifacio E, Gale E A. Antibodies to glutamic acid decarboxylase as predictors of insulin-dependent diabetes mellitus. Lancet. 1994; 344(8917):266-7.

Brice N L, Varadi A, Ashcroft S J, Molnar E. Metabotropic glutamate and GABA(B) receptors contribute to the modulation of glucose-stimulated insulin secretion in pancreatic beta cells. Diabetologia, 2002; 45(2): 242-52.

Cabrera O, Jacques-Silva M C, Speier S, Yang S N, Köhler M, Fachado A, Vieira E, Zierath J R, Kibbey R, Berman D M, Kenyon N S, Ricordi C, Caicedo A, Berggren P O. Glutamate is a positive autocrine signal for glucagon release. Cell Metab. 2008; 7(6):545-54.

Choi D W, Maulucci-Gedde M, Kriegstein A R. Glutamate neurotoxicity in cortical cell culture. *J. Neurosci.*, 1987; 7(2): 357-68.

Choi D W, Koh J Y, Peters S. Pharmacology of glutamate neurotoxicity in cortical cell culture: attenuation by NMDA antagonists. J. Neurosci. 1988; 8(1):185-96.

Danbolt N C. Glutamate uptake. *Prog Neurobiol.*, 2001 September; 65(1): 1-105.

Efrat S, Linde S, Kofod H, Spector D, Delannoy M, Grant S, Hanahan D, Baekkeskov S. Beta-cell lines derived from transgenic mice expressing a hybrid insulin gene-oncogene. *Proc Natl Acad Sci USA.*, 1988; 85(23): 9037-41.

Federici M, Hribal M, Perego L, Ranalli M, Caradonna Z, Perego C, Usellini L, Nano R, Bonini P, Bertuzzi F, Marlier L N, Davalli A M, Carandente O, Pontiroli A E, Melino G, Marchetti P, Lauro R, Sesti G, Folli F. High glucose causes apoptosis in cultured human pancreatic islets of: a potential role for regulation of specific Bcl family genes toward an apoptotic cell death program. Diabetes. 2001; 50(6):1290-301.

Galbiati F, Polastri L, Gregori S, Freschi M, Casorati M, Cavallaro U, Fiorina P, Bertuzzi F, Zerbi A, Pozza G, Adorini L, Folli F, Christofori G, Davalli A M. Antitumorigenic and antiinsulinogenic effects of calcitriol on insulinoma cells and solid beta-cell tumors. Endocrinology. 2002; 143(10):4018-30.

Gillard B K, Thomas J W, Nell L J, Marcus D M. Antibodies against ganglioside GT3 in the sera of patients with type I diabetes mellitus. J. Immunol. 1989; 142(11):3826-32.

Gonoi T, Mizuno N, Inagaki N, Kuromi H, Seino Y, Miyazaki J, Seino S. Functional neuronal ionotropic glutamate receptors are expressed in the non-neuronal cell line MIN6. *J Biol Chem.*, 1994; 269(25): 16989-92. Haas and Erdo, 1991.

Hayashi M, Yamada H, Uehara S, Morimoto R, Muroyama A, Yatsushiro S, Takeda J, Yamamoto A, Moriyama Y. Secretory granule-mediated co-secretion of L-glutamate and glucagon triggers glutamatergic signal transmission in islets of. *J Biol Chem.*, 2003; 278(3): 1966-74.

Hinoi E, Takarada T, Ueshima T, Tsuchihashi Y, Yoneda Y. Glutamate signaling in peripheral tissues. *Eur J. Biochem.*, 2004; 271(1): 1-13.

Hoy M, Maechler P, Efanov A M, Wollheim C B, Berggren P O, Gromada J. Increase in cellular glutamate levels stimulates exocytosis in pancreatic beta-cells. *FEBS Lett.*, 2002; 531(2): 199-203.

Inagaki N, Kuromi H, Gonoi T, Okamoto Y, Ishida H, Seino Y, Kaneko T, Iwanaga T. Seino S. Expression and role of ionotropic glutamate receptors in pancreatic islet cells. *FASEB J.*, 1995; 9(8): 686-91.

Izumi Y, Shimamoto K, Benz A M, Hammerman S B, Olney J W, Zorumski C F. Glutamate transporters and retinal excitotoxicity. Glia. 2002; 39(1):58-68.

Lipton S A, Rosenberg P A Excitatory amino acids as a final common pathway for neurologic disorders. N Engl J. Med. 1994; 330(9):613-22.

Manfras B J, Rudert W A, Trucco M, Boehm B O. Cloning and characterization of a glutamate transporter cDNA from human brain and pancreas. *Biochim Biophys Acta.*, 1994; 1195(1): 185-8.

Matute C, Sánchez-Gómez M V, Martínez-Millán L, Miledi R. Glutamate receptor-mediated toxicity in optic nerve oligodendrocytes. Proc Natl Acad Sci USA. 1997.

Matute C, Alberdi E, Domercq M, Sánchez-Gómez M V, Pérez-Samartín A, Rodríguez-Antigüedad A, Pérez-Cerdá F. Excitotoxic damage to white matter. J Anat. 2007; 210(6): 693-702.

Molnár E, Váradi A, McIlhinney R A, Ashcroft S J. Identification of functional ionotropic glutamate receptor proteins in pancreatic beta-cells and in islets of. FEBS Lett. 1995; 371(3):253-7.

Moriyama Y, Hayashi M. Glutamate-mediated signaling in the islets of: a thread entangled. *Trends Pharmacol Sci.*, 2003; 24(10): 511-7.

Muroyama A, Uehara S, Yatsushiro S, Echigo N, Morimoto R, Morita M, Hayashi M, Yamamoto A, Koh D S, Moriyama Y. A novel variant of ionotropic glutamate receptor regulates somatostatin secretion from delta-cells of islets of. *Diabetes.*, 2004; 53(7): 1743-53.

Nedergaard M, Takano T, Hansen A J. Beyond the role of glutamate as a neurotransmitter. *Nat Rev Neurosci.* 2002; 3(9): 748-55.

Palmer, J. P. Asplin C M, Clemons P, Lyen K, Tatpati O, Raghu P K, Paquette T L Insulin antibodies in insulin-dependent diabetics before insulin treatment. Science., 1983; 222: 1337-1339.

Perego C, Vanoni C, Bossi M, Massari S, Basudev H, Longhi R, Pietrini G. The GLT1 and GLAST glutamate transporters are expressed on morphologically distinct astrocytes and regulated by neuronal activity in primary hippocampal cocultures. *J. Neurochem.*, 2000; 75(3): 1076-84.

Pihoker C, Gilliam L K, Hampe C S, Lernmark A. Autoantibodies in diabetes. Diabetes. 2005; 54 Suppl 2:S52-61.

Powers A C, Efrat S, Mojsov S, Spector D, Habener J F, Hanahan D Proglucagon processing similar to normal islets in pancreatic alpha-like cell line derived from transgenic mouse tumor. *Diabetes.*, 1990; 39(4): 406-14.

Reetz A, Solimena M, Matteoli M, Folli F, Takei K, De Camilli P. GABA and pancreatic beta-cells: colocalization of glutamic acid decarboxylase (GAD) and GABA with synaptic-like microvesicles suggests their role in GABA storage and secretion. *EMBO J.*, 1991; 10(5): 1275-84.

Ricordi C, Lacy P E, Finke E H, Olack B J, Sharp D W: Automated method for isolation of human pancreatic islets. Diabetes 37:413-420, 1988.

Rothstein, J. D., Patel, S., Regan, M. R., Haenggeli, C., Huang, Y. H., Bergles, D. E., Jin, L., Dykes Hoberg, M., Vidensky, S., Chung, D. S., Toan, S. V., Bruijn, L. I., Su, Z. Z., Gupta, P., and Fisher, P. B. Beta-lactam antibiotics offer neuroprotection by increasing glutamate transporter expression. *Nature*, 2005, 433, 73-77

Rothstein J D, Dykes-Hoberg M, Pardo C A, Bristol L A, Jin L, Kuncl R W, Kanai Y, Hediger M A, Wang Y, Schielke J P, Welty D F. Knockout of glutamate transporters reveals a major role for astroglial transport in excitotoxicity and clearance of glutamate. Neuron. 1996; 16(3):675-86.

Rothstein, J. D., Jin, L., Dykes-Hoberg, M., and Kuncl, R. W. Chronic inhibition of glutamate uptake produces a model of slow neurotoxicity. *Proc. Natl. Acad. Sci. U.S.A.*, 1993; 90, 6591-6595

Satin L S, Kinard T A Neurotransmitters and their receptors in the islets of the pancreas: what messages do acetylcholine, glutamate, and GABA transmit? Endocrine. 1998; 8(3):213-2.

Skerry T M, Genever P G. Glutamate signalling in non-neuronal tissues. Trends Pharmacol Sci. 2001; 22(4):174-81.

Solimena M, Folli F, Denis-Donini S, Comi G C, Pozza G, De Camilli P, Vicari A M. Autoantibodies to glutamic acid decarboxylase in a patient with stiff-man syndrome, epilepsy, and type I diabetes mellitus. N Engl J. Med. 1988; 318(16): 1012-20.

Solimena M, Folli F, Aparisi R, Pozza G, De Camilli P. Autoantibodies to GABA-ergic neurons and pancreatic beta cells in stiff-man syndrome. N Engl J. Med. 1990; 322(22): 1555-60.

Storto M, Capobianco L, Battaglia G, Molinaro G, Gradini R, Riozzi B, Di Mambro A, Mitchell K J, Bruno V, Vairetti M P, Rutter G A, Nicoletti F. Insulin secretion is controlled by mGlu5 metabotropic glutamate receptors. *Mol. Pharmacol.*, 2006; 69(4): 1234-41.

Su, Z. Z., Leszczyniecka, M., Kang, D. C., Sarkar, D., Chao, W., Volsky, D. J., and Fisher, P. B. Insights into glutamate transport regulation in human astrocytes: cloning of the promoter for excitatory amino acid transporter 2 (EAAT2). *Proc. Natl. Acad. Sci. U.S.A.* 2003, 100, 1955-1960

Tan, E. M. Autoantibodies in pathology and cell biology. Cell 1991; 67:841-842.

Tanaka K, Watase K, Manabe T, Yamada K, Watanabe M, Takahashi K, Iwama H, Nishikawa T, Ichihara N, Kikuchi T, Okuyama S, Kawashima N, Hori S, Takimoto M, Wada K. Epilepsy and exacerbation of brain injury in mice lacking the glutamate transporter GLT1. Science. 1997; 276(5319): 1699-702.

Tong Q, Ouedraogo R, Kirchgessner A L. Localization and function of group III metabotropic glutamate receptors in rat pancreatic islets. *Am J Physiol Endocrinol Metab.*, 2002; 282(6): E1324-33.

Trotti D, Danbolt N C, Volterra A. Glutamate transporters are oxidant-vulnerable: a molecular link between oxidative and excitotoxic neurodegeneration? Trends Pharmacol Sci. 1998; 19(8):328-34.

Tsui H, Chan Y, Tang L, Winer S, Cheung R K, Paltser G, Selvanantham T, Elford A R, Ellis J R, Becker D J, Ohashi P S, Dosch H M. Targeting of pancreatic glia in type 1 diabetes. Diabetes. 2008; 57(4):918-28.

Utsunomiya-Tate N, Endou H, Kanai Y. Cloning and functional characterization of a system ASC-like Na+-dependent neutral amino acid transporter. J Biol Chem. 1996; 271(25): 14883-90.

Van De Winkel M, Smets G, Gepts W, Pipeleers D. Islet cell surface antibodies from insulin-dependent diabetics bind specifically to pancreatic B cells. J Clin Invest. 1982; 70(1):41-9.

Vanoni C, Massari S, Losa M, Carrega P, Perego C, Conforti L, Pietrini G. Increased internalisation and degradation of GLT1 glial glutamate transporter in a cell model for familial amyotrophic lateral sclerosis (ALS). *J Cell Sci.,* 2004; 117(Pt 22): 5417-26.

Weaver C D, Yao T L, Powers A C, Verdoorn T A. Differential expression of glutamate receptor subtypes in rat pancreatic islets. *J Biol Chem.,* 1996; 271(22): 12977-84.

Weaver C D, Gundersen V, Verdoorn T A. A high affinity glutamate/aspartate transport system in pancreatic islets of modulates glucose-stimulated insulin secretion. *J Biol Chem.,* 1998; 273(3): 1647-53.

Weiss M D, Rossignol C, Sumners C, Anderson K J A pH-dependent increase in neuronal glutamate efflux in vitro: Possible involvement of ASCT1. *Brain Research,* 2005 1056: 105-112.

Wenzlau J M, Juhl K, Yu L, Moua O, Sarkar S A, Gottlieb P, Rewers M, Eisenbarth G S, Jensen J, Davidson H W, Hutton J C. The cation efflux transporter ZnT8 (Slc30A8) is a major autoantigen in human type 1 diabetes. Proc Natl Acad Sci USA. 2007; 104(43):17040-5.

---

The invention claimed is:

1. A method in vitro for identifying type 1 diabetes or LADA (Latent Autoimmune Diabetes in Adults) or susceptibility to type 1 diabetes in a subject, which comprises determining the presence of antibodies reactive to the glutamate transporter protein GLT1 in a blood serum sample of said subject
wherein the presence of antibodies reactive to GLT1 in the serum identifies said subject with type 1 diabetes or LADA or at risk of developing said type 1 diabetes.

2. A method according to claim 1, wherein the GLT1 protein is contacted with the serum sample from a human subject in conditions allowing the formation of an immune complex which is then detected by immunochemical or immunoenzymatic reactions.

3. A method according to claim 1, wherein the presence of antibodies reactive to GLT1 is detected through a functional assay which comprises the following steps:

a) cells expressing GLT1 are incubated with a serum sample in conditions allowing the interaction between GLT1 and antibodies reacting therewith, b) the cell uptake of a labelled GLT1-substrate is measured and compared to the uptake in untreated control cells or in cells treated with a serum sample from non pre-diabetic or non-diabetic subjects, whereby any change in cell uptake in the test sample is indicative of the presence of antibodies reacting with GLT1.

4. A method according to claim 1, which is applied to the screening of individuals affected by diabetes or of subjects at risk of developing diabetes or LADA (Latent Autoimmune Diabetes in Adults).

* * * * *